(12) United States Patent

Vijayendran et al.

(10) Patent No.: US 12,624,121 B2

(45) Date of Patent: May 12, 2026

(54) ASSAYS FOR TIMP2 HAVING IMPROVED PERFORMANCE IN BIOLOGICAL SAMPLES

(71) Applicant: Biomerieux, Inc., Salt Lake City, UT (US)

(72) Inventors: Ravi A. Vijayendran, San Diego, CA (US); Srivatsa Venkatasubbarao, Sammamish, WA (US)

(73) Assignee: bioMerieux, Inc., Salt Lake City, UT (US)

( * ) Notice: Subject to any disclaimer, the term of this patent is extended or adjusted under 35 U.S.C. 154(b) by 466 days.

(21) Appl. No.: 18/339,145

(22) Filed: Jun. 21, 2023

(65) Prior Publication Data

US 2024/0002529 A1 Jan. 4, 2024

Related U.S. Application Data

(62) Division of application No. 16/603,071, filed as application No. PCT/US2018/026058 on Apr. 4, 2018, now Pat. No. 11,718,682.

(60) Provisional application No. 62/482,089, filed on Apr. 5, 2017.

(51) Int. Cl.
*C07K 16/30* (2006.01)
*G01N 33/575* (2026.01)

(52) U.S. Cl.
CPC ..... *C07K 16/3015* (2013.01); *G01N 33/5758* (2026.01); *C07K 2317/20* (2013.01); *C07K 2317/34* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,698,671 A | 12/1997 | Stetler-Stevenson et al. |
| 6,391,265 B1 | 5/2002 | Buechler et al. |
| 6,407,213 B1 | 6/2002 | Carter et al. |
| 7,097,983 B2 | 8/2006 | Markovsky et al. |
| 7,125,493 B2 | 10/2006 | Wang et al. |
| 7,214,542 B2 | 5/2007 | Hutchinson |
| 8,778,615 B2 | 7/2014 | Anderberg et al. |
| 9,360,488 B2 | 6/2016 | Anderberg et al. |
| 9,459,261 B2 | 10/2016 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | Mcpherson et al. |
| 10,457,744 B2 | 10/2019 | Vijayendran et al. |
| 10,457,774 B2 | 10/2019 | Small et al. |
| 2002/0034765 A1 | 3/2002 | Daugherty et al. |
| 2006/0094061 A1 | 5/2006 | Brys et al. |
| 2006/0099684 A1 | 5/2006 | Moses et al. |
| 2007/0031286 A1 | 2/2007 | Miike et al. |
| 2010/0009462 A1 | 1/2010 | Christ et al. |
| 2010/0010201 A1 | 1/2010 | Silbiger et al. |
| 2012/0283128 A1 | 11/2012 | Anderberg et al. |
| 2013/0052655 A1 | 2/2013 | Kobayashi et al. |
| 2013/0157881 A1 | 6/2013 | Anderberg et al. |
| 2014/0377777 A1 | 12/2014 | Anderberg et al. |
| 2015/0086558 A1 | 3/2015 | Chang et al. |
| 2016/0146832 A1 | 5/2016 | Chawla et al. |
| 2016/0257762 A1 | 9/2016 | Kwon et al. |
| 2016/0281083 A1 | 9/2016 | Niitsu et al. |
| 2016/0297893 A1 | 10/2016 | Vijayendran et al. |
| 2017/0199182 A1 | 7/2017 | Lee |
| 2017/0248613 A1 | 8/2017 | Anderberg et al. |
| 2018/0074054 A1 | 3/2018 | Mcpherson et al. |
| 2019/0263926 A1 | 8/2019 | Mcpherson et al. |
| 2019/0302131 A1 | 10/2019 | Mcpherson et al. |
| 2020/0071416 A1 | 3/2020 | Vijayendran et al. |
| 2020/0103415 A1 | 4/2020 | Anderberg et al. |

FOREIGN PATENT DOCUMENTS

| | | |
|---|---|---|
| JP | H05-244985 | 9/1993 |
| JP | 2002-507725 A | 3/2002 |
| JP | 2008-516593 A | 5/2008 |
| WO | WO 1990/11287 | 10/1990 |
| WO | WO 1992/11018 | 7/1992 |
| WO | WO 1996/33735 | 10/1996 |
| WO | WO 1996/34096 | 10/1996 |
| WO | WO 1998/24893 | 6/1998 |
| WO | WO 1999/47930 | 9/1999 |
| WO | WO 2006/010529 | 2/2006 |
| WO | WO 2007/048100 | 4/2007 |

(Continued)

OTHER PUBLICATIONS

Aitken, "Antibody Phage Display," Molecular Biomethods Handbook, 2nd Edition, Humana Press, 2008, pp. 563-564.

Anonymous, "Question (52796): Anti-TIMP2 antibody (ab53730)," Abram, Jun. 29, 2012, Retrieved from the Internet: URL:http:// www.abcam.comITIMP2-antibody-ab53730/questions/52796 [retrieved on Apr. 5, 2017].

Baca et al., "Antibody Humanization Using Monovalent Phage Display," J Biol Chem, Apr. 18, 1997, 272(16):10678-10684.

Baldridge et al., "Monophosphoryl Lipid A (MPL) Formulations for the Next Generation of Vaccines," Methods, 1999, 19:103-107.

(Continued)

*Primary Examiner* — Ellen J Marcsisin

(57) ABSTRACT

The present invention relates to antibodies or antigen binding fragments thereof that binds to human "TIMP2. Further provided are methods for treating subjects, including human subjects, in need of treatment with the isolated TIMP2 antibodies or antigen-binding fragments thereof disclosed herein. Further provided are pharmaceutical or sterile compositions of anti-TIMP2 antibodies and antigen-binding fragments of the invention, the antibody or antigen-binding fragment thereof is admixed with a pharmaceutically acceptable carrier or excipient. Further provided are kits comprising one or more components that include an anti-TIMP2 antibody or antigen-binding fragment thereof of the invention or a pharmaceutical composition thereof.

20 Claims, No Drawings

Specification includes a Sequence Listing.

(56) References Cited

FOREIGN PATENT DOCUMENTS

| | | |
|---|---|---|
| WO | WO 2007/048102 | 4/2007 |
| WO | WO 2010/048346 | 4/2010 |
| WO | WO 2011/047346 | 4/2011 |
| WO | WO 2011/075744 | 6/2011 |
| WO | WO 2011/097539 | 8/2011 |
| WO | WO 2011/162821 | 12/2011 |
| WO | WO 2013/043310 | 3/2013 |
| WO | WO 2013/086359 | 6/2013 |
| WO | WO 2014/031476 | 2/2014 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Bieg et al., "GAD65 and Insulin B Chain Peptide (9-23) are not Primary Autoantigens in the Type 1 Diabetes Syndrome pf the BB Rat," Autoimmunity, 1999, 31:15-24.

Bitter et al., "Expression and Secretion Vectors for Yeast," Methods Enzymol, 1987, 153:516-544.

Bodden et al., "Functional Domains of Human TIMP-1 (Tissue Inhibitor of Metalloproteinases)," J Biol Chem, Jul. 22, 1994, 269(29):18943-18952.

Bradbury et al., "Beyond natural antibodies: the power of in vitro display technologies," Nat Biotechnol, Mar. 2011, 29(3):245-254.

Brown et al., "Antigen retrieval incryostat tissue sections and cultured cells by treatment with sodium dodecyl sulfate (SDS)," Histochem Cell Biol, 1996, 105:261-267.

Brüggemann et al., "Production of human antibody repertoires in transgenic mice," Curr Opin Biotechnol, 1997, 8:455-458.

Campbell, Monoclonal Antibody Technology, Elsevier Sci Publication, 1984, 15 pp.

Carter et al., "Humanization of an anti-p185HER2 antibody for human cancer therapy," Proc Natl Acad Sci USA, May 1992, 89:4285-4289.

Caterina et al., "Inactivating Mutation of the Mouse Tissue Inhibitor of Metalloproteinases-2(Timp-2) Gene Alters ProMMP-2 Activation," J Biol Chem, Aug. 25, 2000, 275(34):26416-26422.

Cockett et al., "High Level Expression of Tissue Inhibitor of Metalloproteinases in Chinese Hamster Ovary Cells Using Glutamine Synthetase Gene Amplification," Biotechnology, Jul. 1990, 8:662-667.

Colbere-Garapin et al., "A New Dominant Hybrid Selective Marker for Higher Eukaryotic Cells," J Mol Biol, 1981, 150:1-14.

Crouse et al., "Expression and Amplification of Engineered Mouse Dihydrofolate Reductase Minigenes," Mol Cell Biol, Feb. 1983, 3:257-266.

Cwirla et al., "Peptides on phage: A vast library of peptides for identifying ligands," Proc Natl Acad Sci USA, Aug. 1990, 87:6378-6382.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, 2002, 169(6):3076-3084.

Devlin et al., "Random Peptide Libraries: A Source of Specific Protein Binding Molecules," Science, 1990, 249:404-406.

Dondelinger et al., "Understanding the Significance and Implications of Antibody Numbering and Antigen-Binding Surface/Residue Definition," Front. Immunol., Oct. 2018, 9:2278, doi: 10.3389/fimmu.2018.02278, 15 pp.

Edwards et al., "The Remarkable Flexibility of the Human Antibody Repertoire; Isolation of Over One Thousand Different Antibodies to a Single Protein, BLyS," J. Mol. Biol., 2003, 334: 103-118.

Eton et al., "Active Immunotherapy with Ultraviolet B-Irradiated Autologous Whole Melanoma Cells plus Detox in Patients with Metastatic Melanoma," Clin Cancer Res, Mar. 1998, 4:619-627.

Fischer et al., "A readers' guide to the interpretation of diagnostic test properties: clinical example of sepsis," Intensive Care Med, 2003, 29:1043-1051.

Foecking et al., "Powerful and versatile enhancer-promoter unit for mammalian expression vectors," Gene, 1986, 45:101-105.

Fujimoto et al., "Determination of tissue inhibitor of metalloproteinases-2 (TIMP-2) in experimental animals using monoclonal antibodies against TIMP-2-specific oligopeptides," Journal of Immunological Methods, 1995, 187:33-39.

Fujimoto et al., "A one-step sandwich enzyme immunoassay for tissue inhibitor of metalloproteinases-2 using monoclonal antibodies," Clinica Chimica Acta, 1993, 220:31-45.

Gorman et al., "Reshaping a therapeutic CD4 antibody," Proc Natl Acad Sci USA, May 1991, 88:4181-4185.

Greene et al., "Molecular Cloning and Characterization of Human Tissue Inhibitor of Metalloproteinase 4," J Biol Them, Nov. 29, 1996, 271(48):30375-30380.

Griffiths et al., "Strategies for selection of antibodies by phage display," Curr Opin Biotechnol. 1998, 9:102-108.

Gupta et al., "Adjuvants for human vaccines—current status, problems and future prospects," Vaccine, 1995, 13(14):1263-1276.

Harlow et al., "Antibodies a Laboratory Manual," Cold Spring Harbor, NY, Cold Spring Harbor Laboratory Press, 1988, pp. 141-155.

He et al., "Humanization and Pharmacokinetics of a Monoclonal Antibody with Specificity for Both E- and P-Selectin," J Immunol, 1998, 160:1029-1035.

Inouye et al.,"Up-promoter mutations in the lpp gene of *Escherichia coli*," Nucleic Acids Res, 1985, 13(9):3101-3110.

Johnson et al., "3-0-Desacyl Monophosphoryl Lipid A Derivatives: Synthesis and Immunostimulant Activities," J Med Chem, 1999, 42:4640-4649.

Jones et al., "Replacing the complementarity-determining regions in a human antibody with those from a mouse," Nature, May 29-Jun. 4, 1986, 321:522-525.

Kohler, "Immunoglobulin chain loss in hybridoma lines," Proc Natl Acad Sci USA, Apr. 1980, 77(4):2197-2199.

Kohler et al., "Continuous cultures of fused cells secreting antibody of predefined specificity," Nature, Aug. 7, 1975, 256:495-497.

Krauss et al., "Specificity grafting of human antibody frameworks selected from a phage display library: generation of a highly stable humanized anti-CD22 single-chain Fv fragment," Protein Eng, 2003, 16(10):753-759.

Larsen et al., "Quantification of Tissue Inhibitor of Metalloproteinases 2 in Plasma from Healthy Donors and Cancer Patients," Scand J Immunol, 2005, 61:449-460.

Lodmell et al., "DNA vaccination of mice against rabies virus: effects of the route of vaccination and the adjuvant monophosphoryl lipid A (MPL)," Vaccine, 2000, 18:1059-1066.

Logan et al., "Adenovirus tripartite leader sequence enhances translation of mRNAs late after infection," Proc Natl Acad Sci USA, Jun. 1984, 81:3655-3659.

Lonberg et al., "Human Antibodies From Transgenic Mice," Intern Rev Immunol, 1995, 13:65-93.

Lowy et al., "Isolation of Transforming DNA: Cloning the Hamster aprt Gene," Cell, Dec. 1980, 22:817-823.

Meyer et al., "New insights in Type I and II CD20 antibody mechanisms-of-action with a panel of novel CD20 antibodies," British Journal of Haematology, 2018, 180:808-820.

Morgan et al., "Human Gene Therapy," Annu Rev Biochem, 1993, 62:191-217.

Morlacchi et al., "Self-antigen presentation by mouse B cells results in regulatory T-cell induction rather than anergy or clonal deletion," Blood, Jul. 28, 2011 , 118(4):984-991.

Mulligan, "The Basic Science of Gene Therapy," Science, May 14, 1993, 260:926-932.

(56)                    References Cited

OTHER PUBLICATIONS

Mulligan et al., "Selection for animal cells that express the *Escherichia coli* gene coding for xanthine-guanine phosphoribasyltransferase," Proc Natl Acad Sci USA, Apr. 1981, 78(4):2072-2076.

Nelson et al., "A computer program for calculating antibody affinity constants," Comput Methods Programs Biomed, 1988, 27:65-68.

Nie et al., "Rapid detection of TIMP-2 in serum of patients with hepatitis by monoclonal antibody double antibody sandwich Elisa," Chinese Journal of Gastroenterology and Hepatology, Dec. 2005, 14(6):577-580 (machine translation).

O'Connor et al., "Humanization of an antibody against human protein C and calcium-dependence involving framework residues," Protein Eng, 1998, 11(4):321-328.

Ofran et al., "Automated Identification of Complementarity Determining Regions (CDRs) Reveals Peculiar Characteristics of CDRs and B Cell Epitopes," J Immunol, 2008, 181(9):6230-6235.

O'Hare et al., "Transformation of mouse fibroblasts to methotrexate resistance by a recombinant plasmid expressing a prokaryotic dihydrofolate reductase," Proc Natl Acad Sci USA, Mar. 1981, 78(3):1527-1531.

Presta et al., "Humanization of an Anti-Vascular Endothelial Growth Factor Monoclonal Antibody for the Therapy of Solid Tumors and Other Disorders," Cancer Res, Oct. 15, 1997, 57:4593-4599.

Proudfoot, "Transcriptional interference and termination between duplicated alpha-globin gene constructs suggests a novel mechanism for gene regulation," Nature, 1986, 322:562-565.

Queen et al., "A humanized antibody that binds to the interleukin 2 receptor," Proc Natl Acad Sci USA, Dec. 1989, 86:10029-10033.

R&D Systems Inc., "Quantikine Elisa Human TIMP-2 Immunoassay," Cat # DTM200, Oct. 1, 2016, KP055361590, retrieved from the Internet: URL:https://resources.mndsystems.com/pdfs/datasheets/dtm200.pdf retrieved on Apr. 4, 2017] (12 pp).

Rader et al., "A phage display approach for rapid antibody humanization: Designed combinatorial V gene libraries," Proc Natl Acad Sci USA, Jul. 1998, 95:8910-8915.

Riechmann et al., "Reshaping human antibodies for therapy," Nature, Mar. 1988, 332:323-327.

Roguska et al., "Humanization of murine monoclonal antibodies through variable domain resurfacing," Proc Natl Acad Sci USA, Feb. 1994, 91:969-973.

Roque et al., "Antibodies and Genetically Engineered Related Molecules: Production and Purification," Biotechnol Prog, 2004, 20:639-654.

Rosok et al., "A Combinatorial Library Strategy for the Rapid Humanization of Anticarcinoma BR96 Fab," J Biol Chem, Sep. 13, 1996, 271(37)22611-22618.

Rossi et al., "A Comparative Study Between a Novel Category of Immunoreagents and the Corresponding Mouse Monoclonal Antibodies," Am J Clin Pathol, 2005, 124:295-302.

Rothe et al., "The Human Combinatorial Antibody Library HuCAL Gold Combines Diversification of All Six CDRs According to the Natural Immune System with a Novel Display Method for Efficient Selection of High-Affinity Antibodies," J Mol Biol, 2008, 376:1182-1200.

Ruther et al., "Easy identification of cDNA clones," EMBO J, 1983, 2(10):1791-1794.

Santerre et al., "Expression of prokaryotic genes for hygromycin B and G418 resistance as dominant-selection markers in mouse L cells," Gene, 1984, 30:147-156.

Scott et al., "Searching for Peptide Ligands with an Epitope Library," Science, 1990, 249:386-390.

Szybalska et al., "Genetics of Human Cell Lines, IV. DNA-Mediated Heritable Transformation of a Biochemical Trait," Proc Natl Acad Sci USA, 1962, 48:2026-2034.

Tachibana et al., "Altered reactivity of immunoglobulin produced by human-human hybridoma cells transfected by pSV2-neo gene," Cytotechnology, 1991, 6:219-226.

Talvensaari-Mattila et al., "Levels of Circulating TIMP-2 and MMP2-TIMP2 Complex Are Decreased in Squamous Cervical Carcinoma," Obstetrics and Gynecology International, Feb. 21, 2010, vol. 2010:179351, 3 pp.

Tan et al., "Superhumanized Antibodies: Reduction of Immunogenic Potential by Complementarity-Determining Region Grafting with Human Germline Sequences: Application to an Anti-CD28," J Immunol, 2002, 169:1119-1125.

Tiller et al., "Advances in Antibody Design," Annu Rev Biomed Eng, 2015;17:191-216 doi: 10.1146/annurev-bioeng-071114-040733.

Tolstoshev, "Gene Therapy, Concepts, Current Trials and Future Directions," Annu Rev Pharmacol Toxicol, 1993, 33:573-596.

Tsurushita et al., "Humanization of Monoclonal Antibodies," Molecular Biology of B Cells, 2004:533-545.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Van Erp et al., "Application of a Sol Particle Immunoassay to the Determination of Affinity Constants of Monoclonal Antibodies," J Immunoassay, 1991, 12(3):425-443.

Van Heeke et al., "Expression of Human Asparagine Synthetase in *Escherichia coli*," J Biol Chem, Apr. 5, 1989, 264(10):5503-5509.

Verhoeyen et al., "Reshaping Human Antibodies: Grafting an Antilysozyme Activity," Science, 1988, 239:1534-1536.

Ward et al., "Binding activities of a repertoire of single immunoglobulin variable domains secreted from *Escherichia coli*," Nature, Oct. 12, 1989, 341:544-546.

Wigler et al., "Transfer of Purified Herpes Virus Thymidine Kinase Gene to Cultured Mouse Cells," Cell, May 1977, 11:223-232.

Wigler et al., "Transformation of mammalian cells with an amplifiable dominant-acting gene," Proc Natl Acad Sci USA, Jun. 1980, 77(6):3567-3570.

Wilson et al., "Simplified conjugation chemistry for coupling peptides to F(ab') fragments: autologous red cell agglutination assay for HIV-1 antibodies," J Immunol Methods, 1994, 175:267-273.

Wu et al., "Humanization of a Murine Monoclonal Antibody by Simultaneous Optimization of Framework and CDR Residues," J Mol Biol, 1999, 294:151-162.

Yarmush et al., "Coupling of antibody-binding fragments to solid-phase supports: site-directed binding of F(ab')2 fragments," J Biochem Biophys Methods, 1992, 25:285-297.

Zucker et al., "Tissue Inhibitor of Metalloproteinase-2 (TIMP-2) Binds to the Catalytic Domain of the Cell Surface Receptor, Membrane Type 1-Matrix Metalloproteinase 1 (MT1-MMP)," J of Biolog Chem, Jan. 9, 1998, 273(2):1216-1222.

Official Action issued Feb. 8, 2023 in Chinese Application No. 201880034638.3.

Copy of International Search Report and Written Opinion issued on Sep. 10, 2018 in PCT/US2018/026058.

Official Action issued Feb. 8, 2022 in Japanese Application No. 2019-554789.

Anne et al., "Levels of Circulating TIMP-2 and MMP2-TIMP2 Complex Are Decreased in Squamous Cervical Carcinoma", Obstet Gynecol Int. 2010;2010:179351. doi: 10.1155/2010/179351. Epub Jun. 29, 2010.

Brown et al. ("Tolerance of single, but not multiple, amino acid replacements in antibody VH CDR 2: a means of minimizing B cell wastage from somatic hypermutation?", J Immunol. May 1996;156(9):3285-91) (Year: 1996).

Extended European Search Report and Written Opinion issued in EP 14834090 dated Apr. 18, 2017.

International Preliminary Report on Patentability issued in PCT/US2014/050195 dated Feb. 18, 2016.

European Search Report and Search Opinion received for European Application No. 18781904.0, mailed on Nov. 5, 2020, 8 pages.

Extended European Search Report and Search Opinion received for European Application No. 19183111.4, mailed on Nov. 11, 2019, 13 pages.

International Preliminary Report on Patentability received for PCT Patent Application No. PCT/US18/26058, mailed on Oct. 17, 2019, 7 pages.

(56) References Cited

OTHER PUBLICATIONS

International Search Report and Written Opinion issued Dec. 16, 2014 in PCT/US2014/050195 (9 pages).

ASSAYS FOR TIMP2 HAVING IMPROVED PERFORMANCE IN BIOLOGICAL SAMPLES

The present application is a divisional application of U.S. patent application Ser. No. 16/603,071 filed Oct. 4, 2019, which is a U.S. National Phase Entry of International Patent Application No. PCT/US2018/026058 filed Apr. 4, 2018, which claims the benefit of U.S. Provisional Patent Application 62/482,089 filed Apr. 5, 2017, which is hereby incorporated by reference in its entirety, including all tables, figures, and claims.

SEQUENCE LISTING

This application contains a Sequence Listing which has been submitted in XML format and is hereby incorporated by reference in its entirety. Said XML copy, created on Jun. 21, 2023, is named ASTM_0005_DV_Sequence_Listing.xml and is 66,735 bytes in size.

BACKGROUND

The following discussion of the background of the invention is merely provided to aid the reader in understanding the invention and is not admitted to describe or constitute prior art to the present invention.

Metalloproteinase inhibitor 2 (Swiss-Prot P16035, also known as "Tissue inhibitor of metalloproteinases 2" and "TIMP2") is a secreted protein which complexes with metalloproteinases and irreversibly inactivates them by binding to their catalytic zinc cofactor. TIMP2 is known to act on MMP-1, MMP-2, MMP-3, MMP-7, MMP-8, MMP-9, MMP-10, MMP-13, MMP-14, MMP-15, MMP-16 and MMP-19. TIMP2 reportedly suppresses the proliferation of endothelial cells. As a result, the encoded protein has been suggested to have a role in the maintenance of tissue homeostasis by suppressing the proliferation of quiescent tissues in response to angiogenic factors, and by inhibiting protease activity in tissues undergoing remodeling.

In addition, WO2010/048346 and WO2011/075744, each of which is hereby incorporated by reference in its entirety including all tables, figures and claims, describe the use of TIMP2 for evaluating the renal status of a subject both individually and in multimarker panels. In particular, TIMP2 levels measured by immunoassay are shown to correlate to risk stratification, diagnosis, staging, prognosis, classifying and monitoring of the renal status. PCT/US2014/050195 discloses certain antibodies for use in such assays.

Signals obtained from specific binding assays such as immunoassays are a direct result of complexes formed between one or more binding species (e.g., antibodies) and the target biomolecule (i.e., the analyte) and polypeptides containing the necessary epitope(s) to which the antibodies bind. Immunoassays are often able to "detect" an analyte; but because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. While such assays may detect the full length biomarker and the assay result be expressed as a concentration of a biomarker of interest, the signal from the assay is actually a result of all such "immunoreactive" polypeptides present in the sample. Such binding assays may also detect immunoreactive polypeptides present in a biological sample that are complexed to additional species, such as binding proteins, receptors, heparin, lipids, sugars, etc., provided that those additional species do not interfere in binding between the binding species and the target biomolecule. Typically, however, specific binding assays are formulated using purified analyte, and complex formation and fragmentation patterns are not considered. This is particularly true where the identity of such additional binding species are unknown.

SUMMARY

It is an object of the invention to provide antibodies which bind novel epitopes of TIMP2. Such antibodies can find use in immunoassays with improved clinical performance, particularly when used in the evaluation of renal injuries, and in therapeutic methods in which TIMP2 binding is desired.

In a first aspect, the present invention relates to antibodies or antigen binding fragments thereof that binds to human TIMP2, wherein the antibody or antigen binding fragment comprises one or more, and optionally each, of:

- a light chain variable region CDR1 comprising the amino acid sequence ESISGW (SEQ ID NO:1) or an amino acid sequence at least 90%, 95%, 97%, 98%, or 99% identical thereto,
- a light chain variable region CDR2 comprising the amino acid sequence RAS (SEQ ID NO:2) or an amino acid sequence at least 90%, 95%, 97%, 98%, or 99% identical thereto,
- a light chain variable region CDR3 comprising the amino acid sequence QCSYGINGNSEHGNP (SEQ ID NO:3) or an amino acid sequence at least 90%, 95%, 97%, 98%, or 99% identical thereto,
- a heavy chain variable region CDR1 comprising the amino acid sequence GFTISSNYY (SEQ ID NO:4) or an amino acid sequence at least 90%, 95%, 97%, 98%, or 99% identical thereto,
- a heavy chain variable region CDR2 comprising the amino acid sequence ILGGSGTYT (SEQ ID NO:5) or an amino acid sequence at least 90%, 95%, 97%, 98%, or 99% identical thereto, and
- a heavy chain variable region CDR3 comprising the amino acid sequence ARQAPADTYLYGGYGPFNL (SEQ ID NO:6) or an amino acid sequence at least 90%, 95%, 97%, 98%, or 99% identical thereto.

In certain embodiments, such antibodies or antigen binding fragments comprise

- a light chain sequence comprising the amino acid sequence of SEQ ID NO:1 or an amino acid sequence at least 90%, 95%, 97%, 98%, or 99% identical thereto; the amino acid sequence of SEQ ID NO:2 or an amino acid sequence at least 90%, 95%, 97%, 98%, or 99% identical thereto; and/or the amino acid sequence of SEQ ID NO:3 or an amino acid sequence at least 90%, 95%, 97%, 98%, or 99% identical thereto; and/or
- a heavy chain sequence comprising the amino acid sequence of SEQ ID NO:4 or an amino acid sequence at least 90%, 95%, 97%, 98%, or 99% identical thereto; the amino acid sequence of SEQ ID NO:5 or an amino acid sequence at least 90%, 95%, 97%, 98%, or 99% identical thereto; and/or the amino acid sequence of SEQ ID NO:6 or an amino acid sequence at least 90%, 95%, 97%, 98%, or 99% identical thereto.

In certain preferred embodiments, such antibodies or antigen binding fragments comprise

- a light chain variable region sequence comprising the amino acid sequence DIVMTQTPSSVEAAVGGTV-TIKCQASESISGWLAWYQQKPGQPPKLLIYR ASTLESGVPSRFKGSGSGTEFTLTISDLECADA-ATYYCQCSYGINGNSEHG NPFGGGTEVVVK (SEQ ID NO: 7) or an amino acid sequence at least 90%, 95%, 97%, 98%, or 99% identical thereto; and/or a heavy chain variable region sequence comprising the amino acid sequence QSLEESGGDLVKPEGSLTLTC-TASGFTISSNYYMCWVRQAPGKGLEWVA CILG-GSGTYTYYATWAKGRFTISKTSSTTVTLQMPSL-TAADTATYFCARQ APADTYLYGGYGPFNLW-GQGTLVTVSS (SEQ ID NO: 8) or an amino acid sequence at least 90%, 95%, 97%, 98%, or 99% identical thereto.

In certain most preferred embodiments, such antibodies or antigen binding fragments comprise a heavy chain variable region sequence comprising the amino acid sequence of SEQ ID NO: 8 and a light chain variable region sequence comprising the amino acid sequence of SEQ ID NO: 7.

In certain most preferred embodiments, such antibodies or antigen binding fragments comprise a heavy chain sequence comprising the amino acid sequence of SEQ ID NO: 10 and a light chain sequence comprising the amino acid sequence of SEQ ID NO:16. Such antibodies are referred to herein as antibody "40H2-40K3."

In still another related aspect, the antibodies or antigen binding fragments described above are a member of a pair of antibodies which form a sandwich complex with a second antibody or antigen binding fragment that also binds to TIMP2. By way of example only, the second antibody may be an antibody described below as 6E2.1 or an antigen binding fragment thereof.

In a related aspect, the present invention relates to antibodies or binding fragments which bind to TIMP2, for example antibody 40H2-40K3, wherein the antibody binds to the sequence NHRYQMGCECKI (SEQ ID NO: 21). Preferred antibodies which bind to this sequence are the antibodies described above, and most preferably such antibodies or antigen binding fragments comprise a heavy chain variable region sequence comprising the amino acid sequence of SEQ ID NO: 8 or an amino acid sequence at least 90%, 95%, 97%, 98%, or 99% identical thereto and a light chain variable region sequence comprising the amino acid sequence of SEQ ID NO: 7 or an amino acid sequence at least 90%, 95%, 97%, 98%, or 99% identical thereto. In certain most preferred embodiments, such antibodies or antigen binding fragments comprise a heavy chain variable region sequence comprising the amino acid sequence of SEQ ID NO: 8 and a light chain variable region sequence comprising the amino acid sequence of SEQ ID NO: 7. Epitope binding is preferably determined by alanine scanning using non-mutated (peptide set 1) and double alanine mutations (peptide set 2) within a nested set of linear 15-mer peptides with a stepping of one amino acid residue derived from the TIMP-2 sequence (SEQ ID NO: 45). See, e.g., McBride et al., Methods Mol. Biol. 1352: 67-83, 2016; Kong et al., J. Virol. 86: 12115-28, 2012.

In certain embodiments, the antibody that binds to the sequence NHRYQMGCECKI (SEQ ID NO: 21) binds to a discontinuous epitope. In these embodiments, the antibodies or binding fragments which bind to TIMP2 further bind to the sequence HPQQAFCNA (SEQ ID NO: 22) and to the sequence RSDGSCAWYR (SEQ ID NO: 23).

In a related aspect, the present invention relates to nucleic acids encoding such antibodies or antigen binding fragments thereof that binds to human TIMP2.

In another aspect, the present invention relates to antibodies or antigen binding fragments thereof that binds to human TIMP2, wherein the antibody or antigen binding fragment comprises one or more, and optionally each, of:

a light chain variable region CDR1 comprising the amino acid sequence DHINNW (SEQ ID NO: 24) or an amino acid sequence at least 90%, 95%, 97%, 98%, or 99% identical thereto, a light chain variable region CDR2 comprising the amino acid sequence SGA (SEQ ID NO: 25) or an amino acid sequence at least 90%, 95%, 97%, 98%, or 99% identical thereto, a light chain variable region CDR3 comprising the amino acid sequence QQYWSTPFT (SEQ ID NO: 26) or an amino acid sequence at least 90%, 95%, 97%, 98%, or 99% identical thereto, a heavy chain variable region CDR1 comprising the amino acid sequence GYSFTSYW (SEQ ID NO: 27) or an amino acid sequence at least 90%, 95%, 97%, 98%, or 99% identical thereto, a heavy chain variable region CDR2 comprising the amino acid sequence IDPSDSET (SEQ ID NO: 28) or an amino acid sequence at least 90%, 95%, 97%, 98%, or 99% identical thereto, and a heavy chain variable region CDR3 comprising the amino acid sequence ARRDYGSRYDAMDY (SEQ ID NO: 29) or an amino acid sequence at least 90%, 95%, 97%, 98%, or 99% identical thereto.

In certain embodiments, such antibodies or antigen binding fragments comprise a light chain sequence comprising the amino acid sequence of SEQ ID NO: 24 or an amino acid sequence at least 90%, 95%, 97%, 98%, or 99% identical thereto; the amino acid sequence of SEQ ID NO: 25 or an amino acid sequence at least 90%, 95%, 97%, 98%, or 99% identical thereto; and/or the amino acid sequence of SEQ ID NO: 26 or an amino acid sequence at least 90%, 95%, 97%, 98%, or 99% identical thereto; and/or a heavy chain sequence comprising the amino acid sequence of SEQ ID NO: 27 or an amino acid sequence at least 90%, 95%, 97%, 98%, or 99% identical thereto; the amino acid sequence of SEQ ID NO: 28 or an amino acid sequence at least 90%, 95%, 97%, 98%, or 99% identical thereto; and/or the amino acid sequence of SEQ ID NO: 29 or an amino acid sequence at least 90%, 95%, 97%, 98%, or 99% identical thereto.

In certain preferred embodiments, such antibodies or antigen binding fragments comprise a light chain variable region sequence comprising the amino acid sequence DIQMTQSSSYLSVSLGGR-VTITCKASDHINNWLAWYQQKPGNAPRLLISG ATSLETGVPSRFSGSGSGKDYTLSITSLQTED-VATYYCQQYWSTPFTFGSG TKLEIK (SEQ ID NO: 30) or an amino acid sequence at least 90%, 95%, 97%, 98%, or 99% identical thereto; and/or a heavy chain variable region sequence comprising the amino acid sequence QVQLQQSGPQLVRPGASVKI-SCKASGYSFTSYWMHWVKQRPGQGLEWIG VI DPSDSETRLNQKFKDKATLTVDKSSSTAY-MQLNSPTSEDSAVYYCARRD Y GSRYDAMDY-WGQGTSVTVSS (SEQ ID NO: 31) or an amino acid sequence at least 90%, 95%, 97%, 98%, or 99% identical thereto.

In certain most preferred embodiments, such antibodies or antigen binding fragments comprise a heavy chain variable region sequence comprising the amino acid sequence of SEQ ID NO: 31 and a light chain variable region sequence comprising the amino acid sequence of SEQ ID NO: 30.

In certain most preferred embodiments, such antibodies or antigen binding fragments comprise a heavy chain sequence comprising the amino acid sequence of SEQ ID NO: 33 and a light chain sequence comprising the amino acid sequence of SEQ ID NO:39. Such antibodies are referred to herein as antibody "6E2.1."

In still another related aspect, the antibodies or antigen binding fragments described above are a member of a pair of antibodies which form a sandwich complex with a second antibody or antigen binding fragment that also binds to TIMP2. By way of example only, the second antibody may be an antibody described above as 40H2-40K3 or an antigen binding fragment thereof.

In a related aspect, the present invention relates to antibodies or binding fragments which bind to TIMP2, for example antibody 6E2.1, wherein the antibody binds to the sequence PWDTLSTTQKK (SEQ ID NO: 44). Preferred antibodies which bind to this sequence are the antibodies described above, and most preferably such antibodies or antigen binding fragments comprise a heavy chain variable region sequence comprising the amino acid sequence of SEQ ID NO: 31 or an amino acid sequence at least 90%, 95%, 97%, 98%, or 99% identical thereto and a light chain variable region sequence comprising the amino acid sequence of SEQ ID NO:30 or an amino acid sequence at least 90%, 95%, 97%, 98%, or 99% identical thereto. In certain most preferred embodiments, such antibodies or antigen binding fragments comprise a heavy chain variable region sequence comprising the amino acid sequence of SEQ ID NO: 31 and a light chain variable region sequence comprising the amino acid sequence of SEQ ID NO: 30. Epitope binding is preferably determined by alanine scanning using single and double alanine mutations within a nested set of linear 15-mer peptides with a stepping of one amino acid residue derived from the TIMP-2 sequence (SEQ ID NO: 45). See, e.g., McBride et al., Methods Mol. Biol. 1352: 67-83, 2016; Kong et al., J. Virol. 86: 12115-28, 2012.

In a related aspect, the present invention relates to nucleic acids encoding such antibodies or antigen binding fragments thereof that binds to human TIMP2.

Antibodies or antigen binding fragments for use in the claimed methods may be obtained from a variety of species. For example, the antibodies or antigen binding fragments of the present invention may comprise immunoglobulin sequences which are rabbit, mouse, rat, guinea pig, chicken, goat, sheep, donkey, human, llama or camelid sequences, or combinations of such sequences (so-called chimeric antibodies). Such antibodies or antigen binding fragments may also be monoclonal or polyclonal. Antibodies for use in the present invention may be identified by their performance in immunoassays, and then further characterized by epitope mapping in order to understand the epitopes which are relevant to that performance. Preferred are rabbit antibodies or humanized versions derived from rabbit antibodies.

Such antibodies or antigen binding fragments may be conjugated to a signal development element or immobilized on a solid support. In addition, such antibodies or antigen binding fragments may be used in a number of competitive and sandwich assay formats. In an example of a sandwich assay, a first antibody or antigen binding fragment (detectably labeled) and a second antibody or antigen binding fragment (immobilized at a predetermined zone of a test device) form sandwich complexes with TIMP2 in the sample at a predetermined zone of a test device. In sandwich assays, the first and second antibodies or antigen binding fragments can be the same (particularly when polyclonal antibodies are used) or different. Thus, the antibodies or antigen binding fragments of the invention may be used in sandwich pairs or may be used individually with another binding entity which is not a monoclonal antibody such as a polyclonal antibody or an aptamer.

The antibodies or antigen binding fragments of the present invention can be used as reagents in test kits for detecting TIMP-2 in biological samples. Such a test kit may, for example, comprise a disposable test device configured to generate a detectable signal related to the present or amount of human TIMP-2 in a biological sample. Alternatively, such a test kit may be formulated for performing an assay in a clinical analyzer which does not utilize a disposable test device. Preferably, the test kit is an in vitro diagnostic. The term "in vitro diagnostic" as used herein refers to a medical device which is a reagent, reagent product, calibrator, control material, kit, instrument, apparatus, equipment, or system, whether used alone or in combination, intended by the manufacturer to be used in vitro for the examination of specimens, including blood and tissue donations, derived from the human body, solely or principally for the purpose of providing information concerning a physiological or pathological state, or concerning a congenital abnormality, or to determine the safety and compatibility with potential recipients, or to monitor therapeutic measures.

In certain embodiments, the immunoassay is performed in a lateral flow format. Lateral flow tests are a form of immunoassay in which the test sample flows in a chromatographic fashion along a bibulous or non-bibulous porous solid substrate. Lateral flow tests can operate as either competitive or sandwich format assays. Preferred lateral flow devices are disposable, single use test devices. A sample is applied to the test device at an application zone and transits the substrate, where it encounters lines or zones which have been pretreated with an antibody or antigen. The term "test zone" as used herein refers to a discrete location on a lateral flow test strip which is interrogated in order to generate a signal related to the presence or amount of an analyte of interest. The detectable signal may be read visually or obtained by inserting the disposable test device into an analytical instrument such as a reflectometer, a fluorometer, or a transmission photometer. This list is not meant to be limiting. Sample may be applied without pretreatment to the application zone, or may be premixed with one or more assay reagents prior to application. In the latter case, the antibody may be provided in a separate container from the disposable test device.

An antibody or antigen binding fragment of the present invention may be diffusively immobilized to a surface within a disposable test device, such that the antibody or antigen binding fragment dissolves into a sample when the sample contacts the surface. In a sandwich assay format, this diffusively bound antibody may bind to its cognate antigen in the sample, and then be immobilized at a detection zone when the antigen is bound by a second antibody or antigen binding fragment non-diffusively bound at the detection zone. In a competitive format, its cognate antigen in the sample may compete for binding to the diffusively bound antibody with a labeled antigen provided as an assay reagent.

A kit of the invention can further comprise a calibration to relate the detectable signal to a concentration of TIMP-2. By way of example, a calibration curve may be provided on an electronic memory device which is read by the analytical instrument which receives the disposable test device, such as a ROM chip, a flash drive, an RFID tag, etc. Alternatively, the calibration curve may be provided on an encoded label which is read optically, such as a 2-D bar code, or transmitted via a network connection. The analytical instrument can then use this calibration curve to relate a detectable signal from an assay into a TIMP-2 concentration In certain embodiment, an assay method performed using one or more antibodies of the present invention provides a signal related to the present or amount of human TIMP-2 in a biological sample, wherein the minimum detectable concentration of TIMP-2 in the assay method is 10 ng/mL or less, more preferably 1 ng/mL or less, and most preferably 0.1 ng/mL or less.

In related aspects, the present invention provides methods for determining the presence or amount of human TIMP2 in a biological sample, comprising:

performing an immunoassay on the biological sample with a first monoclonal antibody or antigen binding fragment and a second monoclonal antibody or antigen binding fragment which together form sandwich complexes with human TIMP2, wherein the immunoassay provides a detectable signal that is related to the presence or amount of human TIMP2 in the biological sample bound in the sandwich complexes; and relating the detectable signal to the presence or amount of human TIMP2 in the biological sample. Preferably, the minimum detectable concentration of TIMP-2 in the immunoassay is 10 ng/mL or less, more preferably 1 ng/mL or less, and most preferably ng/mL or less.

In particularly preferred embodiments, one or both of the first monoclonal antibody or antigen binding fragment and second monoclonal antibody or antigen binding fragment is an antibody of the present invention as described herein. In certain embodiments, the first monoclonal antibody or antigen binding fragment comprises a heavy chain variable region sequence comprising the amino acid sequence of SEQ ID NO: 8 or an amino acid sequence at least 90%, 95%, 97%, 98%, or 99% identical thereto and a light chain variable region sequence comprising the amino acid sequence of SEQ ID NO: 7 or an amino acid sequence at least 90%, 95%, 97%, 98%, or 99% identical thereto, and the second monoclonal antibody or antigen binding fragment comprises a heavy chain variable region sequence comprising the amino acid sequence of SEQ ID NO: 31 or an amino acid sequence at least 90%, 95%, 97%, 98%, or 99% identical thereto and a light chain variable region sequence comprising the amino acid sequence of SEQ ID NO: 30 or an amino acid sequence at least 90%, 95%, 97%, 98%, or 99% identical thereto.

In particularly preferred embodiments, the first monoclonal antibody or antigen binding fragment is 40H2-40K3 or antigen binding fragment thereof and the second monoclonal antibody or antigen binding fragment is 6E2.1 or antigen binding fragment thereof.

Preferred assay methods comprise performing an immunoassay that detects human TIMP-2. Such immunoassays may comprise contacting said body fluid sample with an antibody or antigen binding fragment that detects the marker and detecting binding to that antibody. While the present invention is generally described in terms of immunoassays, other binding entities (e.g., aptamers) which are not based on an immunoglobulin scaffold may be used in lieu of antibodies in such methods. Preferably, the body fluid sample is selected from the group consisting of urine, saliva, blood, serum, and plasma, and most preferably urine.

The details of one or more embodiments of the disclosure are set forth in the accompanying drawings and the description below. Other features, objects, and advantages of the disclosure will be apparent from the description and drawings, and from the claims.

DETAILED DESCRIPTION

Definitions

As used herein, the terms "Metalloproteinase inhibitor 2" and "TIMP-2" refer to one or more polypeptides present in a biological sample that are derived from the Metalloproteinase inhibitor 2 precursor (human precursor: Swiss-Prot P16035 (SEQ ID NO: 45)).

```
          10         20         30         40         50         60
MGAAARTLRL ALGLLLLATL LRPADACSCS PVHPQQAFCN ADVVIRAKAV SEKEVDSGND 70         80         90        100        110        120
IYGNPIKRIQ YEIKQIKMFK GPEKDIEFIY TAPSSAVCGV SLDVGGKKEY LIAGKAEGDG 130        140        150        160        170        180
KMHITLCDFI VPWDILSITQ KKSLNHRYQM GCECKITRCP MIPCYISSPD ECLWMDWVTE 190        200        210        220
KNINGHQAKF FACIKRSDGS CAWYRGAAPP KQEFLDIEDP
```

The following domains have been identified in Metalloproteinase inhibitor 2:

| Residues | Length | Domain ID |
|---|---|---|
| 1-26 | 26 | Signal peptide |
| 27-220 | 194 | Metalloproteinase inhibitor 2 |

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

The term "lateral flow" as used herein refers to flow of reagents in a longitudinal direction through a substantially flat porous material. Such porous material is "substantially flat" if the thickness of the material is no more than 10% of the length and width dimensions.

The term "downstream region" as used herein relative to a first region of a device refers to which receives fluid flow after that fluid has already reached the first region.

The term "sample application region" as used herein refers to a portion of an assay device into which a fluid sample of interest is introduced for purposes of determining a component thereof.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019, 944; 5,985,579; 5,947,124; 5,939,272; 5,922,615; 5,885, 527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react nonspecifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described marker. The kit comprises reagents for the analysis of at least one test sample which comprise at least one antibody that specifically binds to the marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In certain embodiments, the marker assay is performed using a single-use disposable test device. Such test devices often take the form of lateral flow devices which are now familiar from the common use of over-the-counter pregnancy tests. Generally, these assay devices have an extended base layer on which a differentiation can be made between a sample addition region and an evaluation region. In typical use, the sample is applied to the sample addition region, flows along a liquid transport path which runs parallel to the base layer, and then flows into the evaluation region. A capture reagent is present in the evaluation region, and the captured analyte can be detected by a variety of protocols to detect visible moieties associated with the captured analyte. For example, the assay may produce a visual signal, such as color change, fluorescence, luminescence, and the like, when indicating the presence or absence of an analyte in a biological sample.

A sample addition region can be provided, for example, in the form of an open chamber in a housing; in the form of an absorbent pad; etc. The sample addition region can be a port of various configurations, that is, round, oblong, square and the like or the region can be a trough in the device.

A filter element can be placed in, on, or adjacent to the sample addition region to filter particulates from the sample, such as to remove or retard blood cells from blood so that plasma can further travel through the device. Filtrate can then move into a porous member fluidly connected to the filter. Suitable filters for removing or retarding cellular material present in blood are well known in the art. See, e.g., U.S. Pat. Nos. 4,477,575; 5,166,051; 6,391,265; and 7,125, 493, each of which is hereby incorporated by reference in its entirety. Many suitable materials are known to skilled artisans, and can include glass fibers, synthetic resin fibers, membranes of various types including asymmetric membrane filters in which the pore size varies from about 65 to about 15 µm, and combinations of such materials. In addition, a filter element can comprise one or more chemical substances to facilitate separation of red blood cells from blood plasma. Examples of such chemical substances are thrombin, lectins, cationic polymers, antibodies against one or more red blood cell surface antigens and the like. Such chemical substance(s) which facilitate separation of red blood cells from plasma may be provided in the filter element by covalent means, nonspecific absorption, etc.

In certain embodiments, a label zone is located downstream of the sample receiving zone, and contains a diffusively located labeled reagent that binds to the analyte of interest or that competes with the analyte of interest for binding to a binding species. Alternatively, the label zone can be eliminated if the labeled reagent is premixed with the sample prior to application to the sample receiving zone. A detection zone is disposed downstream of from the label zone, and contains an immobilized capture reagent that binds to the analyte of interest.

The optimum pore diameter for the membrane for use in the invention is about 10 to about 50 µm. The membranes typically are from about 1 mil to about 15 mils in thickness, typically in the range of from 5 or 10 mils, but may be up to 200 mils and thicker. The membrane may be backed by a generally water impervious layer, such as a Mylar® polyester film (DuPont Teijin Films). When employed, the backing is generally fastened to the membrane by an adhesive, such as 3M 444 double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used. In various embodiments, the label zone material may be pretreated with a solution that includes blocking and stabilizing agents. Blocking agents include bovine serum albumin (BSA), methylated BSA, casein, nonfat dry milk. The device can also comprise additional components, including for example buffering agents, HAMA inhibitors, detergents, salts (e.g., chloride and/or sulfate salts of calcium, magnesium, potassium, etc.), and proteinaceous components (e.g., serum albumin, gelatin, milk proteins, etc.). This list is not meant to be limiting.

The device may further comprise various control locations which are read to determine that the test device has been run properly. By way of example, a procedural control zone may be provided separate from the assay detection zone to verify that the sample flow is as expected. The control zone is preferably a spatially distinct region at which a signal may be generated that is indicative of the proper flow of reagents. The procedural control zone may contain the analyte of interest, or a fragment thereof, to which excess labeled antibody used in the analyte assay can bind. In operation, a labeled reagent binds to the control zone, even when the analyte of interest is absent from the test sample. The use of a control line is helpful in that appearance of a signal in the control line indicates the time at which the test result can be read, even for a negative result. Thus, when the expected signal appears in the control line, the presence or absence of a signal in the capture zone can be noted. The device may further comprise a negative control area. The purpose of this control area is to alert the user that the test device is not working properly. When working properly, no signal or mark should be visible in the negative control area.

The outer casing or housing of such an assay device may take various forms. Typically, it will include an elongate casing and may have a plurality of interfitting parts. In a particularly preferred embodiment, the housing includes a top cover and a bottom support. The top cover contains an application aperture and an observation port. In a preferred embodiment, the housing is made of moisture impervious solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies may be used to construct a housing. The housing may be prepared by conventional methodologies, such as standard molding technologies that are well known and used in the art. The housing may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, Processes And Materials Of Manufacture, Third Edition, R. A. Lindsberg (1983) Allyn and Baron pp. 393-431.

If necessary, the colorimetric, luminescent, or fluorescent intensity of the detectable label being employed may be then evaluated with an instrument that is appropriate to the label. By way of example, a fluorometer can be used to detect fluorescent labels; a reflectometer can be used to detect labels which absorb light, etc. The concentration of the analyte of interest in the samples may be determined by correlating the measured response to the amount of analyte in the sample fluid.

Assay Correlations

The terms "correlating" and "relating" as used herein in reference to the measurement of biomarkers in an assay refers to determining the presence, or more preferably the amount, of the biomarker in a sample based on the signal obtained from the assay. Often, this takes the form of comparing a signal generated from a detectable label on one species participating in the assay to a predetermined standard curve which can be used to convert the signal to a concentration or threshold amount of the biomarker.

The terms "correlating" and "relating" as used herein in reference to the use of biomarkers for diagnosis or prognosis refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same_patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., Intensive Care Med. 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Preferred therapeutic antibodies are IgG antibodies. The term "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. The known Ig domains in the IgG class of antibodies are VH, Cγ1, Cγ2, Cγ3, VL, and CL. IgG is the preferred class for therapeutic antibodies for several practical reasons. IgG antibodies are stable, easily purified, and able to be stored under conditions that are practical for pharmaceutical supply chains. In vivo they have a long biological half-life that is not just a function of their size but is also a result of their interaction with the so-called Fc receptor (or FcRn). This receptor seems to protect IgG from catabolism within cells and recycles it back to the plasma.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

Antibodies of the invention may be further characterized by epitope mapping, so that antibodies and epitopes may be selected that have the greatest clinical utility in the immunoassays described herein. The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably, an epitope is targeted which is present on the target molecule, but is partially or totally absent on non-target molecules.

In some embodiments, the antibody scaffold can be a mixture of sequences from different species. As such, if the antibody is an antibody, such antibody may be a chimeric antibody and/or a humanized antibody. In general, both "chimeric antibodies" and "humanized antibodies" refer to antibodies that combine regions from more than one species.

For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084.

In one embodiment, the antibody is a fully human antibody. "Fully human antibody" or "complete human antibody" refers to a human antibody having the gene sequence of an antibody derived from a human chromosome. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).
Production of Antibodies Monoclonal antibody preparations can be produced using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Monoclonal antibodies derived from animals other than rats and mice offer unique advantages. Many protein targets relevant to signal transduction and disease are highly conserved between mice, rats and humans, and can therefore be recognized as self-antigens by a mouse or rat host, making them less immunogenic. This problem may be avoided when using rabbit as a host animal. See, e.g., Rossi et al., Am. J. Clin. Pathol., 124, 295-302, 2005.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Adjuvants that can be used in the methods of antibody generation include, but are not limited to, protein adjuvants; bacterial adjuvants, e.g., whole bacteria (BCG, Corynebacterium parvum, Salmonella minnesota) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "GAD65 And Insulin B Chain Peptide (9-23) Are Not Primary Autoantigens In The Type 1 Diabetes Syndrome Of The BB Rat," Autoimmunity, 31(1):15-24, which is incorporated herein by reference), MPL® (Corixa Corporation; See also Lodmell et al. (2000) "DNA Vaccination Of Mice Against Rabies Virus: Effects Of The Route Of Vaccination And The Adjuvant Monophosphoryl Lipid A (MPL)," Vaccine, 18: 1059-1066; Johnson et al. (1999) "3-O-Desacyl Monophosphoryl Lipid A Derivatives: Synthesis And Immunostimulant Activities," Journal of Medicinal Chemistry, 42: 4640-4649; Baldridge et al. (1999)

"Monophosphoryl Lipid A (MPL) Formulations For The Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "Active Immunotherapy With Ultraviolet B-Irradiated Autologous Whole Melanoma Cells Plus DETOX In Patients With Metastatic Melanoma," Clin. Cancer Res. 4(3):619-627; and Gupta et al. (1995) "Adjuvants For Human Vaccines—Current Status, Problems And Future Prospects," Vaccine, 13(14): 1263-1276, both of which are incorporated herein by reference).

Numerous publications discuss the use of phage display technology to produce and screen libraries of polypeptides for binding to a selected analyte. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "Human Antibodies From Transgenic Mice," Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al, 1990, MOLECULAR CLONING, A LABORATORY MANUAL, 2d Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The anti-TIMP2 antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., VH or VL) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

Thus, the present invention includes recombinant methods for making an anti-TIMP2 antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-TIMP2 antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharo-*

*myces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the antibody coding sequence may be ligated individually into the vector in frame with the lac Z coding region so that a fusion protein is produced; pIN vectors (Inouye et al. (1985) "Up-Promoter Mutations In The Lpp Gene Of *Escherichia coli*," Nucleic Acids Res. 13:3101-3110; Van Heeke et al. (1989) "Expression Of Human Asparagine Synthetase In *Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplfiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobutin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY.; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of an antibody of the invention can be increased by vector amplification (for a review, see Bebbington and Hentschel, "The Use Of Vectors Based On Gene Amplification For The Expression Of Cloned Genes In Mammaian Cells," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The anti-TIMP2 antibodies and antigen-binding fragments thereof disclosed herein may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The antibodies and antigen-binding fragments disclosed herein may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies and fragments are conventional and very well known in the art.

Therapeutic Uses of Anti-TIMP2 Antibodies

Further provided are methods for treating subjects, including human subjects, in need of treatment with the isolated antibodies or antigen-binding fragments thereof disclosed herein.

To prepare pharmaceutical or sterile compositions of the anti-TIMP2 antibodies and antigen-binding fragments of the invention (e.g., antibody 6E2.1 or 40H2-40K3 and humanized versions thereof), the antibody or antigen-binding fragment thereof is admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis*

*of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-TIMP2 antibody or antigen-binding fragment thereof of the invention (e.g., antibody 131A or humanized versions thereof) in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-TIMP2 antibodies or antigen-binding fragments thereof of the invention (e.g., antibody 131A and humanized versions thereof) can be administered by an invasive route such as by injection. In further embodiments of the invention, an anti-TIMP2 antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention (e.g., antibody 131A and humanized versions thereof) or a pharmaceutical composition thereof. The present invention also provides an injection device comprising any of the antibodies or antigen-binding fragments of the invention (e.g., antibody 131A and humanized versions thereof) or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-TIMP2 antibody or antigen-binding fragment of the invention (e.g., antibody 131A and humanized versions thereof) in a local rather than systemic manner, for example, via injection of the antibody or fragment directly into a tumor, e.g., a TIMP2⁺ tumor. Furthermore, one may administer the antibody or fragment in a targeted drug delivery system, for example, in a liposome coated with a tissue-specific antibody, targeting, for example, a tumor e.g., a TIMP2⁺ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies may be desirable.

Antibodies or antigen-binding fragments thereof disclosed herein (e.g., antibody 131A and humanized versions thereof) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-TIMP2 antibody in the subject's serum, such as 0.1, 0.3, 1, 3, 10, 30, 100, 300 µg/ml or more. In other embodiments, An anti-TIMP2 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-TIMP2 or antigen-binding fragment thereof of the invention (e.g., antibody 131A and humanized versions thereof) that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Experimental and Diagnostic Uses

The anti-TIMP2 antibodies and antigen-binding fragments thereof disclosed herein may be used as affinity purification agents. In this process, the anti-TIMP2 antibodies and antigen-binding fragments thereof are immobilized on a solid phase such a Sephadex, glass or agarose resin or filter paper, using methods well known in the art. The immobilized antibody or fragment is contacted with a sample containing the TIMP2 protein (or a fragment thereof) to be purified, and thereafter the support is washed with a suitable solvent that will remove substantially all the material in the sample except the TIMP2 protein, which is bound to the immobilized antibody or fragment. Finally, the support is washed with a solvent which elutes the bound TIMP2 (e.g., protein A). Such immobilized antibodies and fragments form part of the present invention.

Further provided are antigens for generating secondary antibodies which are useful for example for performing Western blots and other immunoassays discussed herein.

Anti-TIMP2 antibodies (e.g., humanized antibodies) and antigen-binding fragments thereof may also be useful in diagnostic assays for TIMP2 protein, e.g., detecting its expression in specific cells, tissues, or serum, e.g., tumor cells such as melanoma cells. Such diagnostic methods may be useful in various disease diagnoses.

The present invention includes ELISA assays (enzyme-linked immunosorbent assay) incorporating the use of an anti-TIMP2 antibody or antigen-binding fragment thereof disclosed herein (e.g., antibody 131A or a humanized version thereof).

For example, such a method comprises the following steps:

(a) coat a substrate (e.g., surface of a microtiter plate well, e.g., a plastic plate) with anti-TIMP2 antibody or antigen-binding fragment thereof;

(b) apply a sample to be tested for the presence of TIMP2 to the substrate;

(c) wash the plate, so that unbound material in the sample is removed;

(d) apply detectably labeled antibodies (e.g., enzyme-linked antibodies) which are also specific to the TIMP2 antigen;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

Detection of the label associated with the substrate indicates the presence of the TIMP2 protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., 3H) which can be detected by scintillation counter in the presence of a scintillant.

An anti-TIMP2 antibody or antigen-binding fragment thereof of the invention may be used in a Western blot or immune-protein blot procedure. Such a procedure forms part of the present invention and includes e.g., optionally transferring proteins from a sample to be tested for the presence of TIMP2 (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound TIMP2 or a fragment thereof with an anti-TIMP2 antibody or antigen-binding fragment thereof of the invention; washing the membrane one or more times to remove unbound anti-TIMP2 antibody or fragment and other unbound substances; and detecting the bound anti-TIMP2 antibody or fragment.

Such a membrane may take the form of a nitrocellulose or vinyl-based (e.g., polyvinylidene fluoride (PVDF)) membrane to which the proteins to be tested for the presence of TIMP2 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-TIMP2 antibody or fragment, the membrane is optionally blocked, e.g., with non-fat dry milk or the like so as to bind non-specific protein binding sites on the membrane.

Detection of the bound antibody or fragment indicates that the TIMP2 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-TIMP2 antibodies and antigen-binding fragments thereof disclosed herein may also be used for immunohistochemistry. Such a method forms part of the present invention and comprises, e.g., contacting a cell (e.g., a tumor cell such as a melanoma cell) to be tested for the presence of TIMP2 protein with an anti-TIMP2 antibody or antigen-binding fragment thereof of the invention; and detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-TIMP2 antibodies and antigen-binding fragments thereof disclosed herein may also be used for in vivo tumor imaging. Such a method may include injection of a radiolabeled anti-TIMP2 antibody or antigen-binding fragment thereof into the body of a patient to be tested for the presence of a tumor associated with TIMP2 expression (e.g., which expresses TIMP2, for example, on the tumor cell surface) followed by nuclear imaging of the body of the patient to detect the presence of the labeled antibody or fragment e.g., at loci comprising a high concentration of the antibody or fragment which are bound to the tumor. The detection of the loci indicates the presence of the TIMP2$^+$ tumor and tumor cells.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-TIMP2 antibodies and antigen-binding fragments of the invention, the antibody or antigen-binding fragment thereof is admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-TIMP2 antibody or antigen-binding fragment thereof of the invention in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, intratumoral, or intra-arterial.

In particular embodiments, the anti-TIMP2 antibodies or antigen-binding fragments thereof of the invention can be administered by an invasive route such as by injection. In further embodiments of the invention, an anti-TIMP2 antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention or a pharmaceutical composition thereof. The present invention also provides an injection device comprising any of the antibodies or antigen-binding fragments of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, CaCl$_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-TIMP2 antibody or antigen-binding fragment of the invention in a local rather than systemic manner, for example, via injection of the antibody or fragment directly into a tumor, e.g., a TIMP2$^+$ tumor. Furthermore, one may administer the antibody or fragment in a targeted drug delivery system, for example, in a liposome coated with a tissue-specific antibody, targeting, for example, a tumor e.g., a TIMP2$^+$ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-TIMP2 antibody in the subject's serum, such as 0.1, 0.3, 1, 3, 10, 30, 100, 300 µg/ml or more. In other embodiments, An anti-TIMP2 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-TIMP2 or antigen-binding fragment thereof of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-TIMP2 antibody or antigen-binding fragment, as discussed herein in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-TIMP2 antibody or antigen-binding fragment thereof of the invention or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an anti-TIMP2 antibody or antigen-binding fragment thereof of the invention along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an anti-TIMP2 antibody or antigen-binding fragment thereof of the invention can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-TIMP2 antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-TIMP2 antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-TIMP2 antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-TIMP2 antibody or fragment. In certain embodiments, an anti-TIMP2 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorogenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, NY; Sambrook and Russell (2001) *Molecular Cloning, 3$^{rd}$* ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, NY; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, NY, pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, New York; Kay et al. (1996) *Phage Display of Peptides and Proteins: A Laboratory Manual*, Academic Press, San Diego, CA; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Multispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875); Labrijin et al., Proc. Natl. Acad. Sci. USA 110: 5145-50, 2013; de Jong et al., PLOS Biol 14(1): e1002344, 2016 (doi:10.1371/journal.pbio.1002344). Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry, 2$^{nd}$* ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, OR; Sigma-Aldrich (2003) *Catalogue*, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1: Monoclonal Antibody Development in Rabbits

Female New Zealand Rabbits were immunized by subcutaneous injections (SQ) with antigen/adjuvant emulsions. Primary immunization was done with Complete Freund's Adjuvant and Incomplete Freund's Adjuvant was used for all subsequent boosts. Rabbits were injected SQ every three weeks at 250 µg TIMP2 antigen per rabbit (alternating two sites, hips and scapulas). A test bleed was taken from the marginal ear vein seven days after the second boost. This test bleed (immune sera) was tested by indirect ELISA assay to determine if immune response of the rabbit was adequate for monoclonal antibody development. The best responding rabbit was given a final SQ boost and four days later was euthanized via exsanguination. The whole blood was collected via cardiac puncture. B cells producing antibody of interest were identified by indirect ELISA on target antigen and immunoglobulin genes were isolated. Heavy and light chains were cloned into separate mammalian expression vectors, transfected into HEK cells (transient transfection), and tissue culture supernatant containing rabbit monoclonal antibodies were harvested.

An antibody designated 40H2-40K3 was isolated, and the nucleic acid and protein sequences determined as follows:

```
Heavy chain
                                             SEQ ID NO: 9
atggagactgggctgcgctggcttctcctggtcgctgtgctcaaaggtgtccagtgtcag tcgttggaggagtccgggggagacctggtcaagcctgagggatccctgacactcacctgc acagcctctggattcaccatcagttctaactactacatgtgctgggtccgccaggctcca gggaaggggctggagtgggtcgcatgcattttgggtggtagtggtacttacacttactac gcgacctgggcgaaaggccgattcaccatctccaaaacctcgtcgaccacggtgactctg caaatgcccagtctgacagccgcggacacggccacctatttctgtgcgagacaggcccct gccgatacttatctttatggtggttatggtccctttaacttgtggggccaagggaccctc gtcaccgtctcgagcggacagccgaaagccccgtcggtgtttccactggcgccctgctgt ggcgatacgccttcgtccaccgtgacccttggctgtcttgtgaagggttaccttcccgag ccggtcactgtaacatggaattcagggacactcacgaacggggtcaggactttcccatca gtcagacagtcatccggtctgtattcacttagctcggtagtgtccgtaacttcctccagc cagccggtaacatgtaacgtagcgcaccccgccaccaataccaaggtggacaagaccgtg gcccctcaacatgctcgaaacctacgtgcctccgcctgaacttctcggggggtcccagc gtctttatcttccctcctaagcccaaagatacgctgatgatctcgcggacccccggaggtg acttgtgtcgtggtcgatgtctcccaagacgatcccgaagtacagttcacctggtacatt aacaacgagcaagtccgaacggccaggccaccgttgcgcgagcagcaattcaattcgacg atccgggtggtatcaacgttgccgatcactcatcaggactggttgcAagggaaggaattc aaatgcaaggtccacaacaaggcccttccggcaccaatcgagaaaacgatcagcaaggcg aggggggcagcccctggaacccaaggtctatacaatgggaccacccagggaagagttgtca tcccggtccgtatcgcttacatgcatgattaacggtttctatccttcagacatttcagta gagtgggagaagaatggaaaagccgaagataactacaaaacaaccccccgcagtacttgac tccgacggatcgtacttcttgtacaacaagctctcggtgcccacgtcagaatggcaacga ggggatgtctttacatgctcggtgatgcatgaggcactccacaatcattacacgcagaaa agcatctcccgctcgccgggaaagtgatag SEQ ID NO: 10:
metglrwllllvavlkgvqcqsleesgggdlvkpegsltltctasgftissnyymcwvrqap gkglewvacilggsgtytyyatwakgrftisktssttvtlqmpsltaadtatyfcarqap adtylyggygpfnlwgqgtlvtvssgqpkapsvfplapccgdtpsstvtlgclvkgylpe pvtvtwnsgtltngvrtfpsvrqssglyslssvvsvtsssqpvtcnvahpatntkvdktv apstcskptcpppellggpsvfifppkpkdtlmisrtpevtcvvvdvsqddpevqftwyi nneqvrtarpplreqqfnstirvvstlpithqdwlQgkefkckvhnkalpapiektiska rgqplepkvytmgppreelssrsvsltcmingfypsdisvewekngkaednyktttpavld sdgsyflynklsvptsewqrgdvftcsvmhealhnhytqksisrspgk*
```

The nucleotide and corresponding constant domain amino acid marked as bold and underlined may be replaced, e.g., G>A resulting in amino-acid substitution e.g., R>Q. Preferred residues at this position: R, Q, N.

```
FR1:
                                        (SEQ ID NO: 11)
QSLEESGGDLVKPEGSLTLTCTAS

CDR1:
                                        (SEQ ID NO: 4)
GFTISSNYY

FR2:
                                        (SEQ ID NO: 12)
MCWVRQAPGKGLEWVAC

CDR2:
                                        (SEQ ID NO: 5)
ILGGSGTYT

FR3:
                                        (SEQ ID NO: 13)
YYATWAKGRFTISKTSSTTVTLQMPSLTAADTATYFC

CDR3:
                                        (SEQ ID NO: 6)
ARQAPADTYLYGGYGPFNL

FR4:
                                        (SEQ ID NO: 14)
WGQGTLVTVSS

Light chain
                                        SEQ ID NO: 15:
atggacacgagggcccccactcagctgctggggctcctgctgctctggctcccaggtgcc agatgtgccgacatcgtgatgacccagactccatcctccgtggaggcagctgtgggaggc acagtcaccatcaagtgccaggccagtgagagcattagcggttggttggcctggtatcag cagaaaccagggcagcctcccaagctcctgatctacagggcatccactctggaatctggg gtcccatcgcggttcaaaggcagtggatctgggacagagttcactctcaccatcagcgac ctggagtgtgccgatgctgccacttattattgtcaatgcagttatggtattaatggtaat agtgagcatggtaatcctttcggcggagggaccgaggtggtggtcaaacgtacgcccgtg gcacccactgtactcctgtttccgccttcctcggatgaggtggcgacgggcacggtcaca atcgtctgcgtggcgaataagtactttccggatgtcacagtgacgtgggaggtggacggg acaacacagaccacaggtattgaaaacagcaaaacaccgcagaattcggctgactgtacg tataacttgtcctccactcttacgttgacatcaacacagtacaattcgcacaaggagtat acgtgcaaggtaacccagggtacgacaagcgtagtccagtccttcagcaggaagaactgc tgataa SEQ ID NO: 16
mdtraptqllglllllwlpgarcadivmtqtpssveaavggtvtikcqasesisgwlawyq qkpgqppklliyrastlesgvpsrfkgsgsgteftltisdlecadaatyycqcsygingn sehgnpfgggtevvvkrtpvaptvllfppssdevatgtvtivcvankyfpdvtvtwevdg ttqttgiensktpqnsadctynlsstltltstqynshkeytckvtqgttsvvqsfsrknc FR1:
                                        (SEQ ID NO: 17)
DIVMTQTPSSVEAAVGGTVTIKCQAS

CDR1:
                                        (SEQ ID NO: 1)
ESISGW
```

-continued

```
FR2:
                                        (SEQ ID NO: 18)
LAWYQQKPGQPPKLLIY

CDR2:
                                        (SEQ ID NO: 2)
RAS

FR3:
                                        (SEQ ID NO: 19)
TLESGVPSRFKGSGSGTEFTLTISDLECADAATYYC

CDR3:
                                        (SEQ ID NO: 3)
QCSYGINGNSEHGNP

FR4:
                                        (SEQ ID NO: 20)
FGGGTEVVVK
```

An antibody designated 6E2.1 was isolated, and the nucleic acid and protein sequences determined as follows:

```
Heavy chain
SEQ ID NO 32:
atgggctggagctgcattattctgtttctggtgagcaccgcgaccggcgtgcatagccag gtgcagctgcagcagagcggcccgcagctggtgcgcccgggcgcgagcgtgaaaattagc tgcaaagcgagcggctatagctttaccagctattggatgcattgggtgaaacagcgcccg ggccagggcctggaatggattggcgtgattgatccgagcgatagcgaaacccgcctgaac cagaaatttaaagataaagcgaccctgaccgtggataaaagcagcagcaccgcgtatatg cagctgaacagcccgaccagcgaagatagcgcggtgtattattgcgcgcgccgcgattat ggcagccgctatgatgcgatggattattggggccagggcaccagcgtgaccgtgagcagc gcgaaaaccaccccgccgagcgtgtatccgctggcgccgggcagcgcggcgcagaccaac agcatggtgaccctgggctgcctggtgaaaggctattttccggaaccggtgaccgtgacc tggaac

SEQ ID NO: 33:
MGWSCIILFLVSTATGVHSQVQLQQSGPQLVRPGASVKISCKASGYSFTSYWMHWVKQRP

GQGLEWIGVIDPSDSETRLNQKFKDKATLTVDKSSSTAYMQLNSPTSEDSAVYYCARRDY

GSRYDAMDYWGQGISVTVSSAKTTPPSVYPLAPGSAAQTNSMVTLGCLVKGYFPEPVTVT

WN*

FR1:
                                        (SEQ ID NO: 34)
QSGPQLVRPGASVKISCKAS

CDR1:
                                        (SEQ ID NO: 27)
GYSFTSYW

FR2:
                                        (SEQ ID NO: 35)
MHWVKQRPGQGLEWIGV

CDR2:
                                        (SEQ ID NO: 28)
IDPSDSET

FR3:
                                        (SEQ ID NO: 36)
RLNQKFKDKATLTVDKSSSTAYMQLNSPTSEDSAVYYC

CDR3:
                                        (SEQ ID NO: 29)
ARRDYGSRYDAMDY
```

-continued

```
FR4:
                                      (SEQ ID NO: 37)
WGQGTSVTVSS

Light chain
SEQ ID NO: 38:
atgaaatttccgagccagctgctgctgtttctgctgtttcgcattaccggcattatttgc gatattcagatgacccagagcagcagctatctgagcgtgagcctgggcggccgcgtgacc attacctgcaaagcgagcgatcatattaacaactggctggcgtggtatcagcagaaaccg ggcaacgcgccgcgcctgctgattagcggcgcgaccagcctggaaaccggcgtgccgagc cgctttagcggcagcggcagcggcaaagattataccctgagcattaccagcctgcagacc gaagatgtggcgacctattattgccagcagtattggagcaccccgtttacctttggcagc ggcaccaaactggaaattaaacgcgcggatgcggcgccgaccgtgagcatttttccgccg agcagcgaacagctgagcaac

SEQ ID NO: 39
MKFPSQLLLFLLFRITGIICDIQMTQSSSYLSVSLGGRVTITCKASDHINNWLAWYQQKP

GNAPRLLISGATSLETGVPSRFSGSGSGKDYTLSITSLQTEDVATYYCQQYWSTPFTFGS

GTKLEIKRADAAPTVSIFPPSSEQLSN

FR1:
                                      (SEQ ID NO: 40)
DIQMTQSSSYLSVSLGGRVTITCKAS

CDR1:
                                      (SEQ ID NO: 24)
DHINNW

FR2:
                                      (SEQ ID NO: 41)
LAWYQQKPGNAPRLLI

CDR2:
                                      (SEQ ID NO: 25)
SGA

FR3:
                                      (SEQ ID NO: 42)
TSLETGVPSRFSGSGSGKDYTLSITSLQTEDVATYYC

CDR3:
                                      (SEQ ID NO: 26)
QQYWSTPFT

FR4:
                                      (SEQ ID NO: 43)
FGSGTKLEIK
```

Example 2: Screening of Antibodies with Patient Samples (Microtiter-Based ELISA Method)

Materials:
96-well high bind ELISA plates-Costar 3590 (Corning)
ELISA coating buffer: PBS
ELISA wash buffer: PBS with 0.02% Tween-20
ELISA blocking Buffer (Thermo Pierce, catalogue number N502)
ELISA reagent diluent: 200 mM Tris, 1% BSA (BioFx), 0.05% Tween-20, pH 8.1
Neutravidin-HRP conjugate (Thermo Pierce, catalogue number 31001)
1-Step Ultra TMB substrate (R&D systems, catalogue number 34028)
Stop solution: 2N sulfuric acid
Capture antibodies (6E2.1)
Biotin conjugated detection antibodies (40H2-40K3)
Recombinant human TIMP2 (Peprotech, catalogue number 410-02)

EXLx405 plate washer (Biotek)
Multiskan FC plate reader (Fisher Scientific)
Testing Procedure
Purified, recombinant TIMP2 analyte was spiked into Reagent Diluent and serially diluted to generate a set of standard samples covering a range of concentrations. Frozen single-use aliquots of patient samples were thawed in a room temperature water bath for 10 minutes, and then diluted to desired level with Reagent Diluent.

100 µL of 5 µg/mL Capture Antibody solution prepared in coating buffer was added to each well on a 96-well high bind ELISA plate and incubated over night at room temperature (22° C. to 25° C.). Each well was aspirated and washed three times with 300 µL of wash buffer using an autowasher. Then 250 µL of ELISA blocking buffer was added to each well. After an incubation of 2 hours at room temperature, the aspiration/wash step described above was repeated.

100 µL of standard or patient samples was added to each well of the prepared plate and incubated at room temperature on a horizontal orbital shaker. After 2 hours of incubation, the plate was washed as described above. Then 100 μL of 0.1 μg/mL detection antibody solution prepared in reagent diluent was added to each well. After incubation for 1 hour at room temperature, the plate was washed again. A 0.1 m/mL solution of neutravidin-HRP conjugate was prepared in reagent diluent, and 100 μL of this solution was added to each well. The plate was incubated for 1 hour at room temperature and washed. 100 μL of 1-step ultra TMB substrate was added to each well, incubated at room temperature for 10 minutes protected from light, followed by 50 μL of stop solution. The optical density in each well was measured with a microplate reader set to a wavelength of 450 nm.

Example 3: Screening of Antibodies with Patient Samples (Lateral

Flow Strip Testing Method)
Materials:
    Nitrocellulose membrane
    Backing card
    Sample pad
    Wicking pad
    Membrane blocking buffer: 10 mM Sodium phosphate, 0.1% sucrose, 0.1% BSA, PVP-40, pH 8.0
    Sample pad blocking buffer: 5 mM Borate, 0.1% Tween-20, 0.25% PVP-40, 0.5% BSA, pH 8.5
    Running buffer J: 500 mM Tris, 0.2% 10 G, 0.35% Tween-20, 0.25% PVP-40, pH 8.5
    Fluorescently-conjugated antibodies (40H2-40K3)
    Test line antibodies (6E2.1)
    Goat-anti-mouse positive control antibodies
    Recombinant human TIMP-2
Strip Assembly
    Nitrocellulose membranes were striped with test line antibodies using an AD3050 aspirate dispense system, blocked with the membrane blocking buffer and dried at 37° C. for 30 min. After curing over night in a desiccator, the striped and blocked nitrocellulose membranes were laminated onto backing cards with wicking pads and sample pads pre-treated with the sample pad blocking buffer. The cards were cut into 5 mm wide test strips, which were then placed into cartridges.
Sample Preparation
    Purified, recombinant TIMP-2 analyte was spiked into Running buffer J and serially diluted to generate a set of standard samples covering a range of concentrations. Frozen single-use aliquots of patient samples were thawed in a room temperature water bath for 10 minutes, and then diluted to desired level with Running buffer J.
Testing Procedure
    10 μL of fluorescently conjugated antibody (0.025 μg/μL) in PBS was added to 100 μL of sample. 100 μL of this solution was then loaded into the input port on the cartridge. Results was read at t=20 minutes using a fluorescence reader and associated software.

Example 4: Epitope Mapping Using Pepscan Method Synthesis of Peptides and Pepscan Screening Synthetic linear peptides were synthesized and screened as described by Slootstra et al. (Slootstra et al., 1996, Mol. Diversity 1, 87-96) and Timmerman et al. (Timmerman et al., 2007, J, Mol Recognit 20, 283-299). The binding of antibody to each peptide was tested in a PEPSCAN-based enzyme-linked immuno assay (ELISA). The covalently linked peptides were incubated with sample (for example 1 μg/mL antibody diluted in a PBS solution containing 5% horse serum (vol/vol) and 4% ovalbumin (weight/vol)) and 1% Tween 80 at 4° C. overnight. After washing, the peptides were incubated with Goat-anti-Rabbit HRP (Jackson Immunoresearch) for 1 hour at 25° C., and subsequently, after washing the peroxidase substrate 2,2'-azino-di-3-ethylbenzthiazoline sulfonate (ABTS) and 2 μg/mL 3% $H_2O_2$ were added. After 1 hour the color development was measured.

Peptide set 1 consisted of a nested linear 15-mer peptides from the TIMP-2 sequence having a step of 1 amino acid residue, while peptide set 2 consisted of an identical set of peptides with a double alanine mutant at positions 11 and 12 of the peptide. By way of example, three peptides in peptide set 1, starting from the first residue of native TIMP2 (SEQ ID NO: 45) would be:

```
                                        (SEQ ID NO: 46)
            MGAAARTLRLALGLL (SEQ ID NO: 47)
            GAAARTLRLALGLLL (SEQ ID NO: 48)
            AAARTLRLALGLLLL
```

With the corresponding mutated sequences being:

```
                                        (SEQ ID NO: 49)
            MGAAARTLRLGAGLL (SEQ ID NO: 50)
            GAAARTLRLAAALLL (SEQ ID NO: 51)
            AAARTLRLALAALLL
```

Note that when an alanine is present in the native sequence, it is replaced in the corresponding mutated sequence with a glycine. Peptides that show high binding on Set 1 but not on Set 2 identify critical residues for binding.

Using this methodology, the dominant epitope for the antibody 6E2.1 was identified as $_{132}$PWDTLSTTQKK$_{142}$ (SEQ ID NO: 44), with the underlined residues being the most critical residues.

Antibody 40H$_2$-40K3 exhibited three binding regions $_{145}$NHRYQMGCECKI$_{156}$ (SEQ ID NO: 21), $_{33}$HPQQAFCNA$_{41}$ (SEQ ID NO: 22), and $_{196}$RSDGS-CAWYR$_{205}$ (SEQ ID NO: 23), indicating a likely discontinuous epitope. The core binding region was identified as $_{145}$NHRYQMGCECKI$_{156}$ (SEQ ID NO: 21).

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The use of "or" herein means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. All patents and publications mentioned in the specification are indicative of the levels of those of ordinary skill in the art to which the invention pertains prior to the filing date of the disclosure. Nothing herein is to be construed as an admission that the inventors are not entitled to antedate such disclosure by virtue of prior disclosure.

It will be readily apparent to a person skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A monoclonal antibody that binds to human tissue inhibitor of metalloproteinases 2 (TIMP2) protein, wherein the antibody comprises:

(a) a light chain variable region complementarity determining region 1 (CDR1) comprising the amino acid sequence DHINNW (SEQ ID NO: 24), a light chain variable region CDR2 comprising the amino acid sequence SGA, and a light chain variable region CDR3 comprising the amino acid sequence QQYWSTPFT (SEQ ID NO: 26); and (b) a heavy chain variable region CDR1 comprising the amino acid sequence GYSFTSYW (SEQ ID NO: 27), a heavy chain variable region CDR2 comprising the amino acid sequence IDPSDSET (SEQ ID NO: 28), and a heavy chain variable region CDR3 comprising the amino acid sequence ARRDYGSRYDAMDY (SEQ ID NO: 29).

2. The monoclonal antibody of claim 1, wherein the light chain variable region comprises an amino acid sequence at least 90% identical to that set forth as SEQ ID NO: 30 and the heavy chain variable region comprises an amino acid sequence at least 90% identical to that set forth as SEQ ID NO: 31.

3. The monoclonal antibody of claim 2, wherein the light chain variable region comprises an amino acid sequence set forth as SEQ ID NO: 30 and the heavy chain variable region comprises an amino acid sequence set forth as SEQ ID NO: 31.

4. The monoclonal antibody of claim 1, wherein the light chain comprises an amino acid sequence at least 90% identical to that set forth as SEQ ID NO: 39 and the heavy chain comprises an amino acid sequence at least 90% identical to that set forth as SEQ ID NO: 33.

5. The monoclonal antibody of claim 4, wherein the light chain comprises an amino acid sequence set forth as SEQ ID NO: 39 and the heavy chain comprises an amino acid sequence set forth as SEQ ID NO: 33.

6. The monoclonal antibody of claim 1, wherein the antibody is a rabbit antibody.

7. The monoclonal antibody of claim 1, wherein the antibody is conjugated to a signal development element.

8. The monoclonal antibody of claim 1, wherein the antibody is immobilized on a solid support.

9. The monoclonal antibody of claim 1, wherein one of the first and the second monoclonal antibodies is immobilized on a solid support.

10. A rabbit monoclonal antibody comprising a light chain variable region comprising an amino acid sequence set forth as SEQ ID NO: 30 and a heavy chain variable region comprising an amino acid sequence set forth as SEQ ID NO: 31.

11. A method for determining the presence or amount of human tissue inhibitor of metalloproteinases 2 (TIMP2) protein in a biological sample, the method comprising:

performing an immunoassay on the biological sample with first and second monoclonal antibodies which together form sandwich complexes with human TIMP2 protein, wherein the immunoassay provides a detectable signal that is related to the presence or amount of human TIMP2 protein in the biological sample bound in the sandwich complexes; and relating the detectable signal to the presence or amount of human TIMP2 protein in the biological sample, wherein the first monoclonal antibody comprises:

(a) a light chain variable region complementarity determining region 1 (CDR1) comprising the amino acid sequence DHINNW (SEQ ID NO: 24), a light chain variable region CDR2 comprising the amino acid sequence SGA (SEQ ID NO: 25), and a light chain variable region CDR3 comprising the amino acid sequence QQYWSTPFT (SEQ ID NO: 26); and (b) a heavy chain variable region CDR1 comprising the amino acid sequence GYSFTSYW (SEQ ID NO: 27), a heavy chain variable region CDR2 comprising the amino acid sequence IDPSDSET (SEQ ID NO: 28), and a heavy chain variable region CDR3 comprising the amino acid sequence ARRDYGS-RYDAMDY (SEQ ID NO: 29).

12. The method of claim 11, wherein the first monoclonal antibody comprises a light chain variable region comprising an amino acid sequence at least 90% identical to that set forth as SEQ ID NO: 30 and a heavy chain variable region comprising an amino acid sequence at least 90% identical to that set forth as SEQ ID NO: 31.

13. The method of claim 12, wherein the light chain variable region comprises an amino acid sequence set forth as SEQ ID NO: 30 and the heavy chain variable region comprises an amino acid sequence set forth as SEQ ID NO: 31.

14. The method of claim 11, wherein the first monoclonal antibody comprises a light chain comprising an amino acid sequence at least 90% identical to that set forth as SEQ ID NO: 39 and a heavy chain comprising an amino acid sequence at least 90% identical to that set forth as SEQ ID NO: 33.

15. The method of claim 14, wherein the light chain comprises an amino acid sequence set forth as SEQ ID NO: 39 and the heavy chain comprises an amino acid sequence set forth as SEQ ID NO: 33.

16. The method of claim 11, wherein the first monoclonal antibody is a rabbit antibody.

17. The method of claim 11, wherein one of the first and the second monoclonal antibodies is conjugated to a signal development element.

18. The method of claim 11, wherein the minimum detectable concentration is 10 ng/ml or less.

19. The method of claim 11, wherein the immunoassay is performed in a lateral flow format.

20. The method of claim 11, wherein the immunoassay is performed by applying the biological sample to a disposable test device, and the detectable signal is obtained by inserting the disposable test device into an analytical instrument, wherein the sandwich complexes comprising the first and second antibodies are immobilized for detection in a predetermined zone of the disposable test device, and wherein the analytical instrument detects the immobilized sandwich complexes to provide the detectable signal.

* * * * *

```
                            SEQUENCE LISTING

Sequence total quantity: 51
SEQ ID NO: 1              moltype = AA   length = 6
FEATURE                  Location/Qualifiers
REGION                   1..6
                         note = Synthetic
source                   1..6
                         mol_type = protein
                         organism = synthetic construct
SEQUENCE: 1
ESISGW                                                               6

SEQ ID NO: 2              moltype =    length =
SEQUENCE: 2
000

SEQ ID NO: 3              moltype = AA   length = 15
FEATURE                  Location/Qualifiers
REGION                   1..15
                         note = Synthetic
source                   1..15
                         mol_type = protein
                         organism = synthetic construct
SEQUENCE: 3
QCSYGINGNS EHGNP                                                     15

SEQ ID NO: 4              moltype = AA   length = 9
FEATURE                  Location/Qualifiers
REGION                   1..9
                         note = Synthetic
source                   1..9
                         mol_type = protein
                         organism = synthetic construct
SEQUENCE: 4
GFTISSNYY                                                            9

SEQ ID NO: 5              moltype = AA   length = 9
FEATURE                  Location/Qualifiers
REGION                   1..9
                         note = Synthetic
source                   1..9
                         mol_type = protein
                         organism = synthetic construct
SEQUENCE: 5
ILGGSGTYT                                                            9

SEQ ID NO: 6              moltype = AA   length = 19
```

-continued

```
FEATURE             Location/Qualifiers
REGION              1..19
                    note = Synthetic
source              1..19
                    mol_type = protein
                    organism = synthetic construct
SEQUENCE: 6
ARQAPADTYL YGGYGPFNL                                                  19

SEQ ID NO: 7        moltype = AA  length = 113
FEATURE             Location/Qualifiers
REGION              1..113
                    note = Synthetic
source              1..113
                    mol_type = protein
                    organism = synthetic construct
SEQUENCE: 7
DIVMTQTPSS VEAAVGGTVT IKCQASESIS GWLAWYQQKP GQPPKLLIYR ASTLESGVPS  60
RFKGSGSGTE FTLTISDLEC ADAATYYCQC SYGINGNSEH GNPFGGGTEV VVK        113

SEQ ID NO: 8        moltype = AA  length = 126
FEATURE             Location/Qualifiers
REGION              1..126
                    note = Synthetic
source              1..126
                    mol_type = protein
                    organism = synthetic construct
SEQUENCE: 8
QSLEESGGDL VKPEGSLTLT CTASGFTISS NYYMCWVRQA PGKGLEWVAC ILGGSGTYTY  60
YATWAKGRFT ISKTSSTTVT LQMPSLTAAD TATYFCARQA PADTYLYGGY GPFNLWGQGT  120
LVTVSS                                                             126

SEQ ID NO: 9        moltype = DNA  length = 1410
FEATURE             Location/Qualifiers
misc_feature        1..1410
                    note = Synthetic
source              1..1410
                    mol_type = other DNA
                    organism = synthetic construct
SEQUENCE: 9
atggagactg ggctgcgctg gcttctcctg gtcgctgtgc tcaaaggtgt ccagtgtcag  60
tcgttggagg agtccggggg agacctggtc aagcctgagg gatccctgac actcacctgc  120
acagcctctg gattcaccat cagttctaac tactacatgt gctgggtccg ccaggctcca  180
gggaaggggc tggagtgggt cgcatgcatt ttgggtggta gtggtactta cacttactac  240
gcgacctggg cgaaaggccg attcaccatc tccaaaacct cgtcgaccac ggtgactctg  300
caaatgccca gtctgacagc cgcggacacg gccacctatt tctgtgcgag acaggcccct  360
gccgatactt atctttatgg tggttatggt ccctttaact tgtggggcca agggaccctc  420
gtcaccgtct cgagcggaca gccgaaagcc ccgtcggtgt tccactggc gccctgctgt  480
ggcgatacgc cttcgtccac cgtgaccctt ggctgtcttg tgaagggtta ccttcccgag  540
ccggtcactg taacatggaa ttcagggaca ctcacgaacg gggtcaggac tttcccatca  600
gtcagacagt catccggtct gtattcactt agctcggtac tgtccgtaac ttcctccgag  660
cagccggtaa catgtaacgt agcgcacccc gccaccaata ccaaggtgga caagaccgtg  720
gccccctcaa catgctcgaa acctacgtgc cctccgcctg aacttctcgg gggtcccagc  780
gtctttatct tccctcctaa gcccaaagat acgctgatga tctcgcggac cccggaggtg  840
acttgtgtcg tggtcgatgt ctcccaagac gatcccgaag tacagttcac ctggtacatt  900
aacaacgagc aagtccgaac ggccaggcca ccgttgcgcg agcagcaatt caattcgacg  960
atccgggtgg tatcaacgtt gccgatcact catcaggact ggttgcaagg gaaggaattc  1020
aaatgcaagg tccacaacaa ggcccttccg gcaccaatcg agaaaacgat cagcaaggcg  1080
aggggggcagc ccctggaacc caaggtctat acaatgggac cacccaggga agagttgtca  1140
tcccggtccg tatcgcttac atgcatgatt aacggttct atccttcaga catttcagta  1200
gagtgggaga agaatggaaa agccgaagat aactacaaaa caaccccgc agtacttgac  1260
tccgacggat cgtacttctt gtacaacaag ctctcggtgc ccacgtcaga atggcaacga  1320
ggggatgtct ttacatgctc ggtgatgcat gaggcactcc acaatcatta cacgcagaaa  1380
agcatctccc gctcgccggg aaagtgatag                                   1410

SEQ ID NO: 10       moltype = AA  length = 468
FEATURE             Location/Qualifiers
REGION              1..468
                    note = Synthetic
source              1..468
                    mol_type = protein
                    organism = synthetic construct
SEQUENCE: 10
METGLRWLLL VAVLKGVQCQ SLEESGGDLV KPEGSLTLTC TASGFTISSN YYMCWVRQAP  60
GKGLEWVACI LGGSGTYTYY ATWAKGRFTI SKTSSTTVTL QMPSLTAADT ATYFCARQAP  120
ADTYLYGGYG PFNLWGQGTL VTVSSGQPKA PSVFPLAPCC GDTPSSTVTL GCLVKGYLPE  180
PVTVTWNSGT LTNGVRTFPS VRQSSGLYSL SSVVSVTSSS QPVTCNVAHP ATNTKVDKTV  240
APSTCSKPTC PPPELLGGPS VFIFPPKPKD TLMISRTPEV TCVVVDVSQD DPEVQFTWYI  300
NNEQVRTARP PLREQQFNST IRVVSTLPIT HQDWLQGKEF KCKVHNKALP APIEKTISKA  360
```

```
RGQPLEPKVY TMGPPREELS SRSVSLTCMI NGFYPSDISV EWEKNGKAED NYKTTPAVLD    420
SDGSYFLYNK LSVPTSEWQR GDVFTCSVMH EALHNHYTQK SISRSPGK                 468

SEQ ID NO: 11              moltype = AA  length = 24
FEATURE                    Location/Qualifiers
REGION                     1..24
                           note = Synthetic
source                     1..24
                           mol_type = protein
                           organism = synthetic construct
SEQUENCE: 11
QSLEESGGDL VKPEGSLTLT CTAS                                           24

SEQ ID NO: 12              moltype = AA  length = 17
FEATURE                    Location/Qualifiers
REGION                     1..17
                           note = Synthetic
source                     1..17
                           mol_type = protein
                           organism = synthetic construct
SEQUENCE: 12
MCWVRQAPGK GLEWVAC                                                   17

SEQ ID NO: 13              moltype = AA  length = 37
FEATURE                    Location/Qualifiers
REGION                     1..37
                           note = Synthetic
source                     1..37
                           mol_type = protein
                           organism = synthetic construct
SEQUENCE: 13
YYATWAKGRF TISKTSSTTV TLQMPSLTAA DTATYFC                             37

SEQ ID NO: 14              moltype = AA  length = 11
FEATURE                    Location/Qualifiers
REGION                     1..11
                           note = Synthetic
source                     1..11
                           mol_type = protein
                           organism = synthetic construct
SEQUENCE: 14
WGQGTLVTVS S                                                         11

SEQ ID NO: 15              moltype = DNA  length = 726
FEATURE                    Location/Qualifiers
misc_feature               1..726
                           note = Synthetic
source                     1..726
                           mol_type = other DNA
                           organism = synthetic construct
SEQUENCE: 15
atggacacga gggcccccac tcagctgctg gggctcctgc tgctctggct cccaggtgcc    60
agatgtgccg acatcgtgat gacccagact ccatcctccg tggaggcagc tgtgggaggc   120
acagtcacca tcaagtgcca ggccagtgag agcattagcg gttggttggc ctggtatcag   180
cagaaaccag ggcagcctcc caagctcctg atctacaggg catccactct ggaatctggg   240
gtcccatcgc ggttcaaagg cagtggatct gggacagagt tcactctcac catcagcgac   300
ctggagtgtg ccgatgctgc cacttattat tgtcaatgca gttatggtat taatggtaat   360
agtgagcatg gtaatccttt cggcggaggg accgaggtgg tggtcaaacg tacgcccgtg   420
gcacccactg tactcctgtt tccgccttcc tcggatgagg tggcgacggg cacggtcaca   480
atcgtctgcg tggcgaataa gtactttccg gatgtgcaca tgacgtggga ggtggacggg   540
acaacacaga ccacaggtat tgaaaacagc aaaacaccgc agaattcggc tgactgtacg   600
tataacttgt cctccactct tacgttgaca tcaacacagt acaattcgca caaggagtat   660
acgtgcaagg taacccaggg tacgacaagc gtagtccagt ccttcagcag gaagaactgc   720
tgataa                                                              726

SEQ ID NO: 16              moltype = AA  length = 240
FEATURE                    Location/Qualifiers
REGION                     1..240
                           note = Synthetic
source                     1..240
                           mol_type = protein
                           organism = synthetic construct
SEQUENCE: 16
MDTRAPTQLL GLLLLWLPGA RCADIVMTQT PSSVEAAVGG TVTIKCQASE SISGWLAWYQ    60
QKPGQPPKLL IYRASTLESG VPSRFKGSGS GTEFTLTISD LECADAATYY CQCSYGINGN   120
SEHGNPFGGG TEVVVKRTPV APTVLLFPPS SDEVATGTVT IVCVANKYFP DVTVTWEVDG   180
TTQTTGIENS KTPQNSADCT YNLSSTLTLT STQYNSHKEY TCKVTQGTTS VVQSFSRKNC   240

SEQ ID NO: 17              moltype = AA  length = 26
```

-continued

```
FEATURE                 Location/Qualifiers
REGION                  1..26
                        note = Synthetic
source                  1..26
                        mol_type = protein
                        organism = synthetic construct
SEQUENCE: 17
DIVMTQTPSS VEAAVGGTVT IKCQAS                                     26

SEQ ID NO: 18           moltype = AA  length = 17
FEATURE                 Location/Qualifiers
REGION                  1..17
                        note = Synthetic
source                  1..17
                        mol_type = protein
                        organism = synthetic construct
SEQUENCE: 18
LAWYQQKPGQ PPKLLIY                                               17

SEQ ID NO: 19           moltype = AA  length = 36
FEATURE                 Location/Qualifiers
REGION                  1..36
                        note = Synthetic
source                  1..36
                        mol_type = protein
                        organism = synthetic construct
SEQUENCE: 19
TLESGVPSRF KGSGSGTEFT LTISDLECAD AATYYC                          36

SEQ ID NO: 20           moltype = AA  length = 10
FEATURE                 Location/Qualifiers
REGION                  1..10
                        note = Synthetic
source                  1..10
                        mol_type = protein
                        organism = synthetic construct
SEQUENCE: 20
FGGGTEVVVK                                                       10

SEQ ID NO: 21           moltype = AA  length = 12
FEATURE                 Location/Qualifiers
REGION                  1..12
                        note = Synthetic
source                  1..12
                        mol_type = protein
                        organism = synthetic construct
SEQUENCE: 21
NHRYQMGCEC KI                                                    12

SEQ ID NO: 22           moltype = AA  length = 9
FEATURE                 Location/Qualifiers
REGION                  1..9
                        note = Synthetic
source                  1..9
                        mol_type = protein
                        organism = synthetic construct
SEQUENCE: 22
HPQQAFCNA                                                        9

SEQ ID NO: 23           moltype = AA  length = 10
FEATURE                 Location/Qualifiers
REGION                  1..10
                        note = Synthetic
source                  1..10
                        mol_type = protein
                        organism = synthetic construct
SEQUENCE: 23
RSDGSCAWYR                                                       10

SEQ ID NO: 24           moltype = AA  length = 6
FEATURE                 Location/Qualifiers
REGION                  1..6
                        note = Synthetic
source                  1..6
                        mol_type = protein
                        organism = synthetic construct
SEQUENCE: 24
DHINNW                                                           6
```

```
SEQ ID NO: 25           moltype =    length =
SEQUENCE: 25
000

SEQ ID NO: 26           moltype = AA   length = 9
FEATURE                 Location/Qualifiers
REGION                  1..9
                        note = Synthetic
source                  1..9
                        mol_type = protein
                        organism = synthetic construct
SEQUENCE: 26
QQYWSTPFT                                                          9

SEQ ID NO: 27           moltype = AA   length = 8
FEATURE                 Location/Qualifiers
REGION                  1..8
                        note = Synthetic
source                  1..8
                        mol_type = protein
                        organism = synthetic construct
SEQUENCE: 27
GYSFTSYW                                                           8

SEQ ID NO: 28           moltype = AA   length = 8
FEATURE                 Location/Qualifiers
REGION                  1..8
                        note = Synthetic
source                  1..8
                        mol_type = protein
                        organism = synthetic construct
SEQUENCE: 28
IDPSDSET                                                           8

SEQ ID NO: 29           moltype = AA   length = 14
FEATURE                 Location/Qualifiers
REGION                  1..14
                        note = Synthetic
source                  1..14
                        mol_type = protein
                        organism = synthetic construct
SEQUENCE: 29
ARRDYGSRYD AMDY                                                    14

SEQ ID NO: 30           moltype = AA   length = 107
FEATURE                 Location/Qualifiers
REGION                  1..107
                        note = Synthetic
source                  1..107
                        mol_type = protein
                        organism = synthetic construct
SEQUENCE: 30
DIQMTQSSSY LSVSLGGRVT ITCKASDHIN NWLAWYQQKP GNAPRLLISG ATSLETGVPS  60
RFSGSGSGKD YTLSITSLQT EDVATYYCQQ YWSTPFTFGS GTKLEIK               107

SEQ ID NO: 31           moltype = AA   length = 121
FEATURE                 Location/Qualifiers
REGION                  1..121
                        note = Synthetic
source                  1..121
                        mol_type = protein
                        organism = synthetic construct
SEQUENCE: 31
QVQLQQSGPQ LVRPGASVKI SCKASGYSFT SYWMHWVKQR PGQGLEWIGV IDPSDSETRL  60
NQKFKDKATL TVDKSSSTAY MQLNSPTSED SAVYYCARRD YGSRYDAMDY WGQGTSVTVS  120
S                                                                 121

SEQ ID NO: 32           moltype = DNA   length = 546
FEATURE                 Location/Qualifiers
misc_feature            1..546
                        note = Synthetic
source                  1..546
                        mol_type = other DNA
                        organism = synthetic construct
SEQUENCE: 32
atgggctgga gctgcattat tctgtttctg gtgagcaccg cgaccggcgt gcatagccag  60
gtgcagctgc agcagagcgg cccgcagctg gtgcgcccgg gcgcgagcgt gaaaattagc  120
tgcaaagcga gcggctatag ctttaccagc tattggatgc attgggtgaa acagcgcccg  180
ggccagggcc tggaatggat tggcgtgatt gatccgagcg atagcgaaac ccgcctgaac  240
```

-continued

```
cagaaattta aagataaagc gaccctgacc gtggataaaa gcagcagcac cgcgtatatg   300
cagctgaaca gcccgaccag cgaagatagc gcggtgtatt attgcgcgcg ccgcgattat   360
ggcagccgct atgatgcgat ggattattgg ggccagggca ccagcgtgac cgtgagcagc   420
gcgaaaacca ccccgccgag cgtgtatccg ctggcgccgg gcagcgcggc gcagaccaac   480
agcatggtga ccctgggctg cctggtgaaa ggctattttc cggaaccggt gaccgtgacc   540
tggaac                                                              546
```

```
SEQ ID NO: 33              moltype = AA  length = 182
FEATURE                    Location/Qualifiers
REGION                     1..182
                           note = Synthetic
source                     1..182
                           mol_type = protein
                           organism = synthetic construct
SEQUENCE: 33
MGWSCIILFL VSTATGVHSQ VQLQQSGPQL VRPGASVKIS CKASGYSFTS YWMHWVKQRP   60
GQGLEWIGVI DPSDSETRLN QKFKDKATLT VDKSSSTAYM QLNSPTSEDS AVYYCARRDY   120
GSRYDAMDYW GQGTSVTVSS AKTTPPSVYP LAPGSAAQTN SMVTLGCLVK GYFPEPVTVT   180
WN                                                                  182
```

```
SEQ ID NO: 34              moltype = AA  length = 20
FEATURE                    Location/Qualifiers
REGION                     1..20
                           note = Synthetic
source                     1..20
                           mol_type = protein
                           organism = synthetic construct
SEQUENCE: 34
QSGPQLVRPG ASVKISCKAS                                                20
```

```
SEQ ID NO: 35              moltype = AA  length = 17
FEATURE                    Location/Qualifiers
REGION                     1..17
                           note = Synthetic
source                     1..17
                           mol_type = protein
                           organism = synthetic construct
SEQUENCE: 35
MHWVKQRPGQ GLEWIGV                                                   17
```

```
SEQ ID NO: 36              moltype = AA  length = 38
FEATURE                    Location/Qualifiers
REGION                     1..38
                           note = Synthetic
source                     1..38
                           mol_type = protein
                           organism = synthetic construct
SEQUENCE: 36
RLNQKFKDKA TLTVDKSSST AYMQLNSPTS EDSAVYYC                            38
```

```
SEQ ID NO: 37              moltype = AA  length = 11
FEATURE                    Location/Qualifiers
REGION                     1..11
                           note = Synthetic
source                     1..11
                           mol_type = protein
                           organism = synthetic construct
SEQUENCE: 37
WGQGTSVTVS S                                                         11
```

```
SEQ ID NO: 38              moltype = DNA  length = 441
FEATURE                    Location/Qualifiers
misc_feature               1..441
                           note = Synthetic
source                     1..441
                           mol_type = other DNA
                           organism = synthetic construct
SEQUENCE: 38
atgaaatttc cgagccagct gctgctgttt ctgctgtttc gcattaccgg cattatttgc   60
gatattcaga tgacccagag cagcagctat ctgagcgtga gcctgggcgg ccgcgtgacc   120
attacctgca aagcgagcga tcatattaac aactggctgg cgtggtatca gcagaaaccg   180
ggcaacgcgc cgcgcctgct gattagcggc gcgaccagcc tggaaaccgg cgtgccgagc   240
cgctttagcg gcagcggcag cggcaaagat tataccctga gcattaccag cctgcagacc   300
gaagatgtgg cgacctatta ttgccagcag tattggagca ccccgtttac ctttggcagc   360
ggcaccaaac tggaaattaa acgcgcggat gcggcgccga ccgtgagcat ttttccgccg   420
agcagcgaac agctgagcaa c                                             441
```

```
SEQ ID NO: 39              moltype = AA  length = 147
FEATURE                    Location/Qualifiers
```

-continued

```
REGION                  1..147
                        note = Synthetic
source                  1..147
                        mol_type = protein
                        organism = synthetic construct
SEQUENCE: 39
MKFPSQLLLF LLFRITGIIC DIQMTQSSSY LSVSLGGRVT ITCKASDHIN NWLAWYQQKP        60
GNAPRLLISG ATSLETGVPS RFSGSGSGKD YTLSITSLQT EDVATYYCQQ YWSTPFTFGS       120
GTKLEIKRAD AAPTVSIFPP SSEQLSN                                           147

SEQ ID NO: 40           moltype = AA   length = 26
FEATURE                 Location/Qualifiers
REGION                  1..26
                        note = Synthetic
source                  1..26
                        mol_type = protein
                        organism = synthetic construct
SEQUENCE: 40
DIQMTQSSSY LSVSLGGRVT ITCKAS                                             26

SEQ ID NO: 41           moltype = AA   length = 16
FEATURE                 Location/Qualifiers
REGION                  1..16
                        note = Synthetic
source                  1..16
                        mol_type = protein
                        organism = synthetic construct
SEQUENCE: 41
LAWYQQKPGN APRLLI                                                        16

SEQ ID NO: 42           moltype = AA   length = 37
FEATURE                 Location/Qualifiers
REGION                  1..37
                        note = Synthetic
source                  1..37
                        mol_type = protein
                        organism = synthetic construct
SEQUENCE: 42
TSLETGVPSR FSGSGSGKDY TLSITSLQTE DVATYYC                                 37

SEQ ID NO: 43           moltype = AA   length = 10
FEATURE                 Location/Qualifiers
REGION                  1..10
                        note = Synthetic
source                  1..10
                        mol_type = protein
                        organism = synthetic construct
SEQUENCE: 43
FGSGTKLEIK                                                               10

SEQ ID NO: 44           moltype = AA   length = 11
FEATURE                 Location/Qualifiers
REGION                  1..11
                        note = Synthetic
source                  1..11
                        mol_type = protein
                        organism = synthetic construct
SEQUENCE: 44
PWDTLSTTQK K                                                             11

SEQ ID NO: 45           moltype = AA   length = 220
FEATURE                 Location/Qualifiers
REGION                  1..220
                        note = Synthetic
source                  1..220
                        mol_type = protein
                        organism = synthetic construct
SEQUENCE: 45
MGAAARTLRL ALGLLLLATL LRPADACSCS PVHPQQAFCN ADVVIRAKAV SEKEVDSGND        60
IYGNPIKRIQ YEIKQIKMFK GPEKDIEFIY TAPSSAVCGV SLDVGGKKEY LIAGKAEGDG       120
KMHITLCDFI VPWDTLSTTQ KKSLNHRYQM GCECKITRCP MIPCYISSPD ECLWMDWVTE       180
KNINGHQAKF FACIKRSDGS CAWYRGAAPP KQEFLDIEDP                             220

SEQ ID NO: 46           moltype = AA   length = 15
FEATURE                 Location/Qualifiers
REGION                  1..15
                        note = Synthetic
source                  1..15
                        mol_type = protein
```

```
                         organism = synthetic construct
SEQUENCE: 46
MGAAARTLRL ALGLL                                                15

SEQ ID NO: 47           moltype = AA  length = 15
FEATURE                 Location/Qualifiers
REGION                  1..15
                        note = Synthetic
source                  1..15
                        mol_type = protein
                        organism = synthetic construct
SEQUENCE: 47
GAAARTLRLA LGLLL                                                15

SEQ ID NO: 48           moltype = AA  length = 15
FEATURE                 Location/Qualifiers
REGION                  1..15
                        note = Synthetic
source                  1..15
                        mol_type = protein
                        organism = synthetic construct
SEQUENCE: 48
AAARTLRLAL GLLLL                                                15

SEQ ID NO: 49           moltype = AA  length = 15
FEATURE                 Location/Qualifiers
REGION                  1..15
                        note = Synthetic
source                  1..15
                        mol_type = protein
                        organism = synthetic construct
SEQUENCE: 49
MGAAARTLRL GAGLL                                                15

SEQ ID NO: 50           moltype = AA  length = 15
FEATURE                 Location/Qualifiers
REGION                  1..15
                        note = Synthetic
source                  1..15
                        mol_type = protein
                        organism = synthetic construct
SEQUENCE: 50
GAAARTLRLA AALLL                                                15

SEQ ID NO: 51           moltype = AA  length = 15
FEATURE                 Location/Qualifiers
REGION                  1..15
                        note = Synthetic
source                  1..15
                        mol_type = protein
                        organism = synthetic construct
SEQUENCE: 51
AAARTLRLAL AALLL                                                15
```